(12) United States Patent
Kipps et al.

(10) Patent No.: US 9,217,040 B2
(45) Date of Patent: Dec. 22, 2015

(54) THERAPEUTIC ANTIBODIES AGAINST ROR-1 PROTEIN AND METHODS FOR USE OF SAME

(75) Inventors: Thomas J. Kipps, San Diego, CA (US); George F. Widhopf, II, San Diego, CA (US); Bing Cui, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/997,934

(22) PCT Filed: Jan. 13, 2012

(86) PCT No.: PCT/US2012/021339
§ 371 (c)(1),
(2), (4) Date: Jun. 27, 2013

(87) PCT Pub. No.: WO2012/097313
PCT Pub. Date: Jul. 19, 2012

(65) Prior Publication Data
US 2013/0273073 A1    Oct. 17, 2013

Related U.S. Application Data

(60) Provisional application No. 61/433,043, filed on Jan. 14, 2011.

(51) Int. Cl.
*C07K 16/40* (2006.01)
*C07K 16/28* (2006.01)
*A61K 39/00* (2006.01)

(52) U.S. Cl.
CPC ............ *C07K 16/40* (2013.01); *C07K 16/2803* (2013.01); *A61K 2039/505* (2013.01); *C07K 2317/565* (2013.01); *C07K 2317/73* (2013.01); *C07K 2317/77* (2013.01); *C07K 2317/92* (2013.01)

(58) Field of Classification Search
CPC ............ C07K 16/40; C07K 16/2803; C07K 2317/565; C07K 2317/73; C07K 2317/77; A61K 2039/505
See application file for complete search history.

(56) References Cited

U.S. PATENT DOCUMENTS 8,212,009 B2    7/2012    Kipps et al.
2010/0062005 A1    3/2010    Kipps et al.

FOREIGN PATENT DOCUMENTS

WO    WO 2011/054007 A1    5/2011

OTHER PUBLICATIONS

Brown et al., Tolerance of single, but not multiple, amino acid replacements in antibody VH CDR 2: a means of minimizing B cell wastage from somatic hypermutation? J. Immunology 156: 3285-3291, 1996.*
Vajdos et al., Comprehensive functional maps of the antigen-binding site of an anti-ErbB2 antibody obtained with shotgun scanning mutagenesis. J. Mol. Biol. 320:415-428, 2002.*
Rudikoff et al., Single amino acid substitution altering antigen-binding specificity. Proc. Natl. Acad. Sci. USA 79:1979-1983, 1982.*
Paul, William, Fundamental Immunology, 3rd Edition, Raven Press, New York, 1993, pp. 292-295.*
Choudhury et al., "Silencing of *ROR1* and *FMOD* with siRNA Results in Apoptosis of CLL Cells," *Br. J. Haematol.* (2010), 151:327-335, Blackwell Publishing Ltd.
Daneshmanesh et al., "Ror1, a Cell Surface Receptor Tyrosine Kinase is Expressed in Chronic Lymphocytic Leukemia and May Serve as a Putative Target for Therapy," *Int. J. Cancer* (2008), 123:1190-1195, Wiley-Liss, Inc.
Yang et al., "Therapeutic Potential and Challenges of Targeting Receptor Tyrosine Kinase ROR1 with Monoclonal Antibodies in B-Cell Malignancies," *PLoS One* (2011), 6(6):e21018, 1-14, Blackwell Science Ltd.
Fukuda, Tetsuya et al: "*Antisera induced by infusions of autologous Ad-CD154-leukemia B cells identify ROR1 as an oncofetal, antigen and receptor for Wnt5a*", Proceedings of the National Academy of Sciences, National Academy of Sciences, 105(8), Feb. 26, 2008, pp. 3047-3052.
Extended European Search Report Regarding EP 12 734 733.4.

* cited by examiner

*Primary Examiner* — Ruixiang Li
(74) *Attorney, Agent, or Firm* — Mintz, Levin, Cohn, Ferris, Glovsky and Popeo, P.C.

(57) ABSTRACT

Therapeutic antibodies having binding specificity for ROR-1 expressed on cancer cells (particularly leukemic and lymphomic cells) and pharmaceutical compositions containing one or more such antibodies for use in treating cancer. Methods for diagnosing such cancers through in vitro detection of binding to ROR-1 protein expressed on putative cancer cells are also provided.

9 Claims, 25 Drawing Sheets

Comparison of 4A5 Ig Heavy Chain to The Closest
Germline Mouse and Human IGHV

```
                     FR1-IMGT                    CDR1-IMGT                  FR2-IMGT
                      (1-26)                      (27-38)                   (39-55)
              1         10        20          30            40         50
              EVKLVESGG.GLVKPGGSLKLSCAAS  GFTF.....SSYA  MSWVRQIPEKRLEWVAS
4A5_VH
MuIGHV5-09*02 .........................  ....A.......D  .................T
HuIGHV3-48*01 .......Q......Q..R.......  ........S..N  ....A.G.G....SY

CDR2-IMGT                           FR3-IMGT
                  (56-65)                            (66-104)
              60        70        80        90        100
              ISRG...GTT YYPDSVK.GRFTISRDNVRNILYLQMSSLRSEDTAMYYCGR
4A5_VH
MuIGHV5-09*02 ...S....SY. ........A.T...............L...A.
HuIGHV3-48*01 ...SS..SS.I ..A........AK.S....N...A....V....A.
```

FIG. 5

Comparison of 2-G6 Ig Heavy Chain to The Closest
Germline Mouse and Human IGHV

```
                    FR1-IMGT              CDR1-IMGT                FR2-IMGT
                     (1-26)                (27-38)                 (39-55)
                1         10         20         30         40         50
2-G6_QED_VH    EVQLQQSGP.ELEKPGASVKISCKAS GFAF....TGYN MNWVKQTNGKSLEWIGS
MuIGHV1-39*01   .F........................ ....YS...... ............
HuIGHV1-02*02   Q...V..A..VK.......V...... ....YT....Y .H.R.AP.QG...M.W

CDR2-IMGT                      FR3-IMGT
                    (56-65)                        (66-104)
                60         70         80         90         100
G6_QED_VH      IDPY..YGGS TYNQKFK.DKATLTVDKSSSTAYMQLKSLTSDDSAVYYCAR
MuIGHV1-39*01  .N.N.. TT S.......G......Q......N...S.........
HuIGHV1-02*02  .N.N..S..T N.A...Q.GRV.M.R.T.I....E.SR.R...T......
```

FIG. 6

Comparison of 2-G3 Ig Heavy Chain to The Closest
Germline Mouse and Human IGHV

```
                FR1-IMGT                CDR1-IMGT              FR2-IMGT
                (1-26)                   (27-38)                (39-55)
            1         10        20           30          40          50
            QVQLQQPGQ.ELVKPGTSVKLSCKAS  GYNF.....TNYW  INWVKLRPGQGLEWIGE
2-G3_VH     ..........................  ....T.......  .................
MuIGHV1-55*01 .....A..M................  ....T.......  .........T...Q..D
HuIGHV1-46*01 .V.S...VK..A..V..........  ....T...S.Y   MH..RQA......M.I

CDR2-IMGT              FR3-IMGT
            (56-65)                (66-104)
                  60        70        80        90        100
            IYPG..SGST  NYNEKFK.SKATLTADTSSSTAYMQLSSLASEDSALYYCAR
G3_VH       ..........  .........................................
MuIGHV1-55*01 ..........  ..........V..............T....V..........
HuIGHV1-46*01 .N.S...G..  S.AQ..Q.GRV.M.R...T.V.E...R...T.V........
```

FIG. 7

Comparison of 3-H10 Ig Heavy Chain to The Closest
Germline Mouse and Human IGHV

```
                    FR1-IMGT              CDR1-IMGT           FR2-IMGT
                    (1-26)                (27-38)             (39-55)
            1        10        20         30        40        50
3-H10_VH    EVKLVESGG.GLVKPGGSLKLSCAAS GFAF.....TGYN MNWVKQTNGKSLEWIGS
MuIGHV5-9*02 ........................  ..A.........  ................T
HuIGHV3-23*04 ...Q.............Q..R... ............  .....A.G.G....SA

FR3-IMGT
                              (66-104)
            60        70        80        90        100
            CDR2-IMGT
            (56-65)
H10_VH      ISTG...AST YFPDSVK.GRFTISRDNARNILYLQMSSLRSEDTAMYYCAR
MuIGHV5-9*02 ...S...G... .Y...............T...............L.......
HuIGHV3-23*04 ..GS..GG... .YA..............SK.T....N..A....V....K
```

FIG. 8

Human and Murine ROR1 Proteins are Highly Conserved

| Region | Position | # of different aa |
|---|---|---|
| Ig-like | 1---147aa | 12 |
| Linker between Ig-like and CRD | 148---165aa | 1 |
| CRD | 166---299aa | 1 |
| Linker between CRD and Kringle | 300---312aa | 0 |
| Kringle | 313---391aa | 1 |
| Linker between Kringle and TM | 392---406aa | 0 |

Domain Structure and Sequence Homology
of Human and Murine ROR1 Extracellular Protein

```
hROR1   MHRPRRRGTRPPLLALLAALLLAARGAAAQETELSVSAELVPTSSWNISSELNKDSYLTLDEPMNNITTSLGQTAELHCK   80
mROR1   ..........P...................D.................T...ID.G...................... 
                                                                        Ig Domain
hROR1   VSGNPPPTIRWFKNDAPVVQEPRRLSFRSTIYGSRLRIRNLDTTDTGYFQCVATNGKEVVSSTGVLFVKFGPPPTASPGY  160
mROR1   .........S..................I..A.N.....................K...T................S. 
                                                Cysteine Rich Domain
hROR1   SDEYEDGFCQPYRGIACARFIGNRTVYMESLHMQGEIENQITAAFTMIGTSSHLSDKCSQFAIPSLCHYAFPYCDETSS  240
mROR1   ................................................................................

hROR1   VPKPRDLCRDECEILENVLCQTEYIFARSNPMILMRLKLPNCEDLPQPESPEAANCIRIGIPMADPINKNHKCYNSTGVD  320
mROR1   .................V..............................................................
                                        Kringle
hROR1   YRGTVSVTKSGRQCQPWNSQYPHTHTFTALRFPELNGGHSYCRNPGNQKEAPWCFTLDENFKSDLCDIPACDSKDSKEKN  400
mROR1   .................S..............................................................

hROR1   KMEILY
mROR1   ......
```

FIG. 11

Anti-ROR1 Mabs Generated Across Extracellular Domain

| No. | Binding sites of antibodies | | | |
|---|---|---|---|---|
| | 5'-Ig-like | Middle of Ig-like | 3'-Ig-like | CRD | Kringle |
| 1-4A5 | | ✓ | | | |
| G11 | | ✓ | | | |
| H11 | | ✓ | | | |
| 2G3 | | ✓ | | | |
| 3-D10 | | | ✓ | | |

FIG. 12

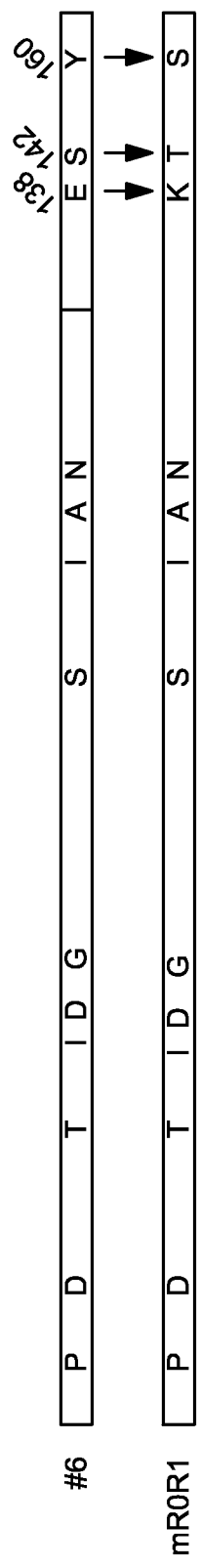
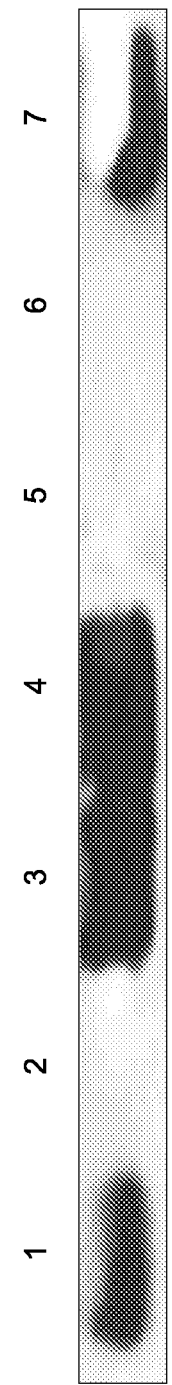
FIG. 15

3-D10 Kd Determination

Analysis(x)

Baseline / Endpoints:
5 to 10 [sec] from beginning
10 to 5 [sec] from end

| Ignore | Binding Signal (V) | Concentration |
|---|---|---|
| | 0.0499 | 500nM |
| | 0.0805 | 250nM |
| | 0.1525 | 125nM |
| | 0.2084 | 62.5nM |
| | 0.2405 | 31.25nM |
| | 0.4173 | 15.63nM |
| | 0.4760 | 7.81nM |
| | 0.5175 | 3.90nM |
| | 0.5015 | 1.95nM |
| | 0.5390 | 976.56pM |
| | 0.5496 | 488.28pM |
| | 0.5581 | 0 |
| ✓ | 0.0012 | 0 |
| | 0.0082 | 500nM |
| | 0.0777 | 250nM |
| ✓ | 0.1245 | 125nM |
| ✓ | 0.1684 | 62.5nM |
| | 0.2908 | 31.25nM |
| | 0.3642 | 15.63nM |
| | 0.4170 | 7.81nM |
| | 04595 | 3.90nM |
| | 0.4782 | 1.95nM |
| | 0.4804 | 976.56pM |
| | 0.4870 | 488.28pM |
| | 0.4968 | 0 |
| ✓ | 0.0049 | 0 |

Kd = 40.47nM
ABC = 40.47pM
Ratio = 0.0010
Sig 100% = 0.54
Drift (%/run) = 0.7514
NSB = 0.00
Drift (mV/run) = -0.7086
%Error = 0.92

Kd = 40.47nM
95% confidence interval
Kd High = 43.50nM
Kd Low = 26.25nM

ABC = 40.47pM
95% confidence interval
ABC High = 0.70nM
ABC Low = Less than 146.19fM

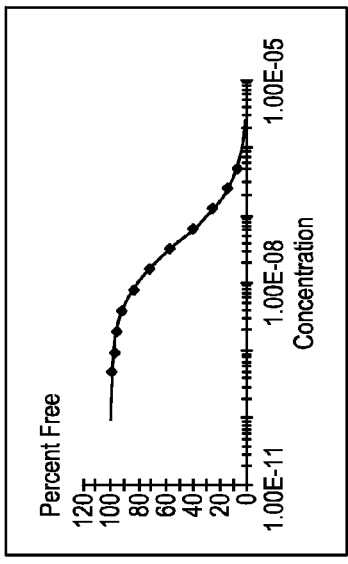
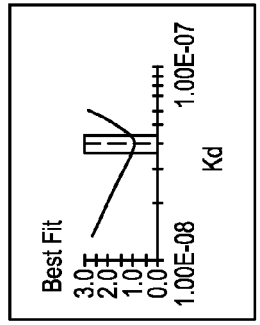
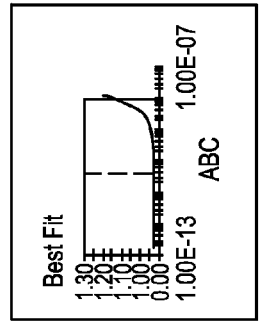

FIG. 16A

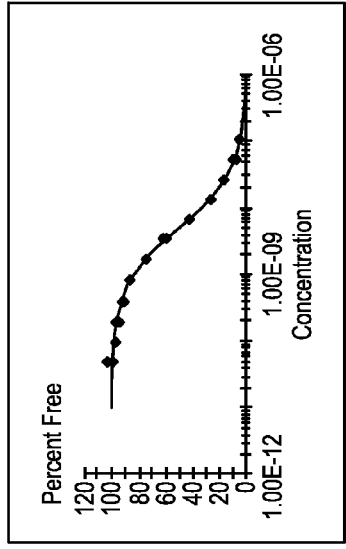
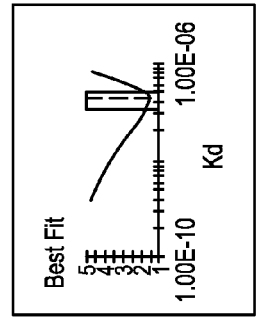
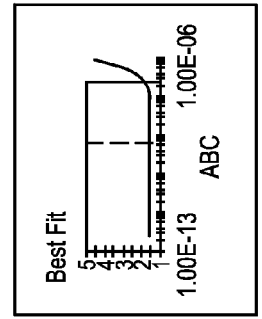
FIG. 16B

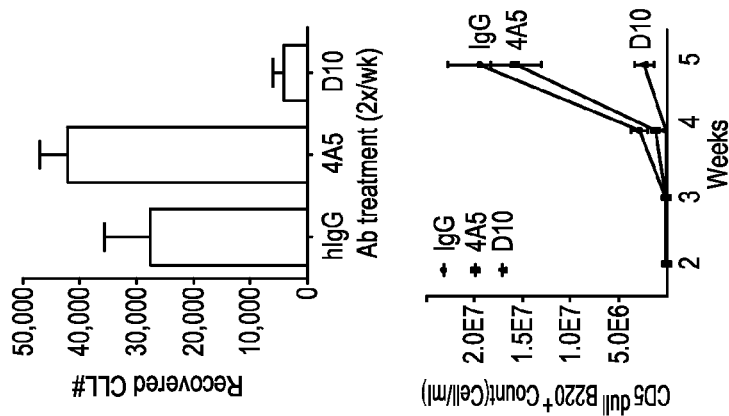

3-D10 Anti-ROR1 mAb is Highly Active in *in vivo* Assays

- 3-D10 Mab highly active in *in vivo* niche dependent activity model
  - Substantial reduction in leukemic burden using 4 primary CLL patient products tested in 76 mice
  - Activity much greater than other anti-ROR1 Mabs (4A5)

- 3-D10 Mab active in *in vivo* immune competent mouse model
  - Substantial reduction in spontaneous human ROR1 expressing leukemia model
  - Activity much greater than other anti-ROR1 Mabs (4A5)

3-D10 Mab has greatest anti-ROR1 activity in *in vivo* assay systems

FIG. 17

THERAPEUTIC ANTIBODIES AGAINST ROR-1 PROTEIN AND METHODS FOR USE OF SAME

CROSS-REFERENCE TO RELATED APPLICATIONS

This application is a 35 USC §371 National Stage application of International Application No. PCT/US2012/021339 filed Jan. 13, 2012, which claims the benefit under 35 USC §119(e) to U.S. Application Ser. No. 61/433,043 filed Jan. 14, 2011, now expired. The disclosure of each of the prior applications is considered part of and is incorporated by reference in the disclosure of this application.

GRANT INFORMATION

This invention was made with government support under Grant No. CA081534 awarded by the National Institutes of Health. The government has certain rights in the invention.

BACKGROUND

Tyrosine kinases are important mediators of the signaling cascade, determining key roles in diverse biological processes like growth, differentiation, metabolism and apoptosis in response to external and internal stimuli. Studies have implicated the role of tyrosine kinases in the pathophysiology of cancer. Schlessinger J. (2000) Cell, 103:211-225; and Robinson et al. (2000) Oncogene, 19:5548-5557. MacKeigan and colleagues used a large-scale RNAi approach to identify kinases that might regulate survival and apoptosis of a human tumor cell line (HeLa), RNAi to ROR1 was found as one of the most potent in inducing apoptosis among the set of RNAi targeting each of 73 different kinase-encoding genes. MacKeigan et al. (2005) Nat Cell Biol., 7:591-600. However, these investigators did not examine the expression or function of ROR1 protein in these cells.

ROR1, receptor tyrosine kinase like orphan receptor one, is a molecule expressed at high levels during embryogenesis that plays a major role in the development of the skeleton, lungs and nervous system. ROR1 expression is greatly decreased in postpartum mammalian cells to levels that are barely detectable. ROR1 is a membrane-receptor with an intracellular kinase-like domain and extracellular Frizzled-like cysteine-rich domain, which is common to receptors of members of the Wnt-family. ROR1 is member of the ROR family that is evolutionarily conserved among *Caenorhavditis elegans, Drosophila*, mice and humans. Wilson C, Goberdhan D C, Steller H. Dror, a potential neurotrophic receptor gene, encodes a Drosophila homolog of the vertebrate Ror family of Trk-related receptor tyrosine kinases. Proc Natl Acad Sci USA. 1993; 90:7109-7113; Oishi et al. (1997) J Biol Chem., 272:11916-11923; Masiakowski et al. (1992) J Biol Chem., 267:26181-26190; Forrester et al. (2002) Cell Mol Life Sci., 59:83-96; and Oishi et al. (1999) Genes Cells, 4:41-56. The actual functional role of the ROR1 protein during embryogenesis is unknown, although it is believed to be a receptor for Wnt proteins that regulate cellular polarity and cell-to-cell interactions.

Although principally an embryonic protein, ROR1 is expressed uniquely on certain cancer cells, including in CLL, small lymphocytic lymphoma, marginal cell B-Cell lymphoma, Burkett's Lymphoma, and other cancers (e.g., breast cancers), but not on normal adult tissues and cells. In a recent study, it was found that ROR1, at both mRNA and protein level, was highly expressed in CLL B cells but not normal B cells. Moreover, it was found that ROR1 is a receptor for Wnt5a, which could induce activation of NF-κB when co-expressed with ROR1 in HEK293 cells and enhance survival of CLL cells in vitro. This indicates that ROR1 is a CLL survival-signaling receptor for Wnt5a. Another study found that ROR1 was expressed in acute lymphocytic leukemia (ALL) as well. Shabani et al. (2007) Tumour Biol., 28:318-326; and Baskar et al. (2008) Clin Cancer Res., 14:396-404. Expression of ROR1 protein has now been demonstrated on a variety of hematologic and solid tumor cancers.

Therapeutic control of ROR1 expression is necessary. However, although polyclonal anti-ROR1 antibodies raised against ROR1 peptide are commercially available. The inventors developed a monoclonal anti-ROR1 antibody, terms 4A5, which reacts with the native ROR1 protein and is capable of detecting cell-surface expression of ROR1 for flow cytometric analysis. However, robustly therapeutic antibodies with demonstrable ability to inhibit ROR-1 mediated cancer cell proliferation to a degree that is therapeutically significant for slowing or preventing growth and metastasis have not been available.

SUMMARY OF THE INVENTION

The invention provides antibodies and combination of antibodies for in vivo and in vitro inhibition of ROR-1 cell mediated proliferation of cells from subjects with cancer, including lymphomas, CLL, small lymphocytic lymphoma, marginal cell B-Cell lymphoma, Burkett's Lymphoma, renal cell carcinoma, colon cancer, colorectal cancer, breast cancer, epithelial squamous cell cancer, melanoma, myeloma, stomach cancer, brain cancer, lung cancer, pancreatic cancer, cervical cancer, ovarian cancer, liver cancer, bladder cancer, prostate cancer, testicular cancer, thyroid cancer, and head and neck cancer, but not in blood or splenic lymphocytes of nonleukemic patients or normal adults.

The antibodies of the invention are also useful for differentiation between ROR1 expressing cancer cells ("ROR1 cancer") and normal cells. For example, an immunoassay that detects ROR1 in a sample from a subject by contacting the sample with a ROR1-specific antibody of the invention and detecting immunoreactivity between the antibody and ROR1 in the sample is provided.

In accordance with a further aspect of the invention, a ROR1 cancer is diagnosed in a subject by detecting the presence or quantity of ROR1 protein in a sample.

The present invention includes compositions that include purified, isolated monoclonal antibodies and combinations thereof that bind specifically to ROR1 receptor protein.

Tg mouse were adoptively transferred i.v. All mice were subsequently monitor weekly for expansion of $CD5^+B220^{low}$ leukemic B cells by flow cytometry beginning at 2 weeks post transfer.

Figure 1:
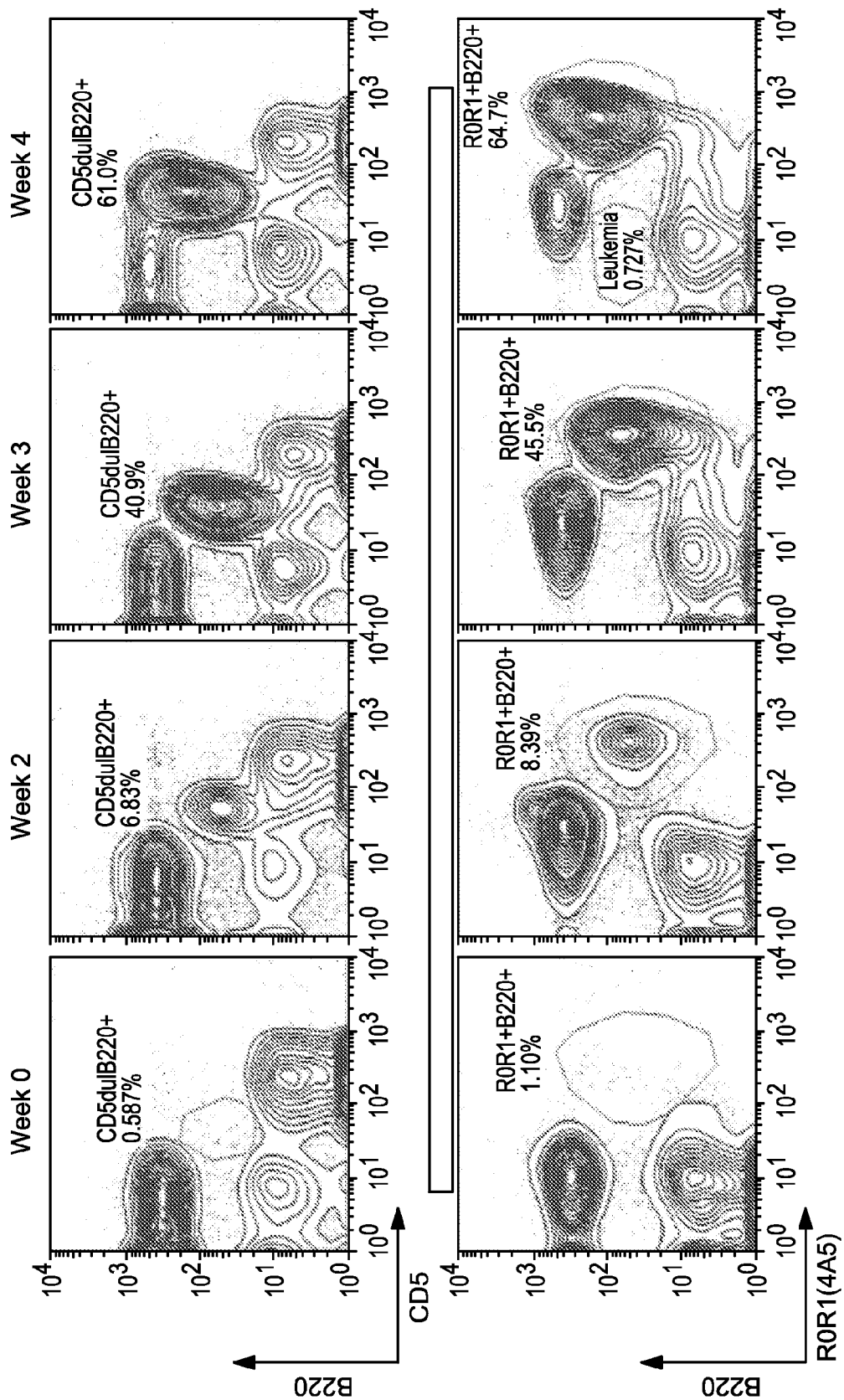
FIG. 1 is a series of graphs illustrating the results of flow cytometric analysis of the expansion of CD5+B220low leukemia B cells in ROR1 Tg mice following the adoptive transfer of $1 \times 10^7$ splenocytes from a ROR1 xTCL1 Tg mouse. Upper panel depicts the expansion from 2 to 4 weeks following adoptive transfer. Percentage of leukemic cells on the contour plot of mCD5 (x-axis) vs mB220 (y-axis) is indicated on above the gate on $CD5^+B220^{low}$ lymphocytes. Bottom panel depicts the relative ROR1 expression (x axis) using the mouse anti-ROR1 4A5 mAb.
Figure 2:
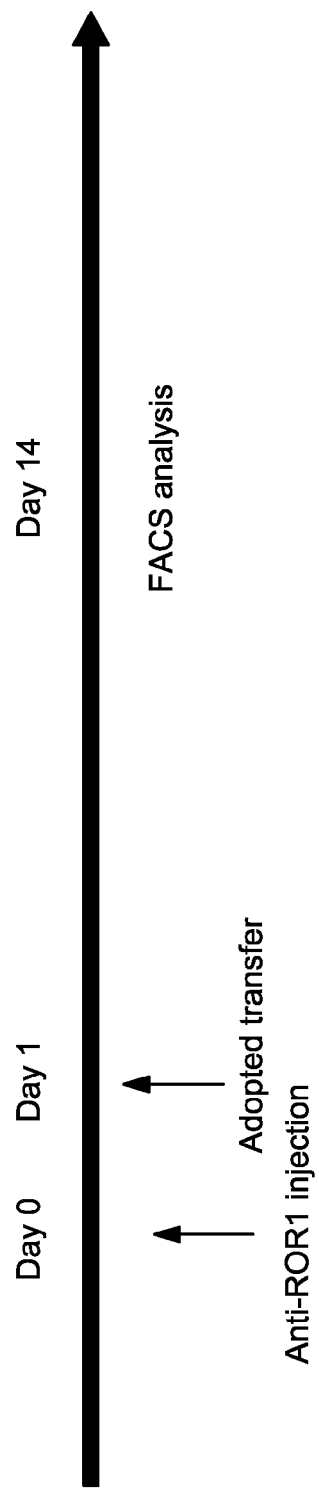
FIG. 2 is a diagram outlining the analysis of anti-ROR1 mAb on the adoptive transfer and engragment of ROR1 XTCL1 leukemic splenocytes. ROR1 Tg mice (4 mice/group) were given 250 ug of 4A5, D10 or control mIgG i.v. on day 0. The following day, $1 \times 10^7$ splenocytes from a ROR1 x TCL1
Figure 3:
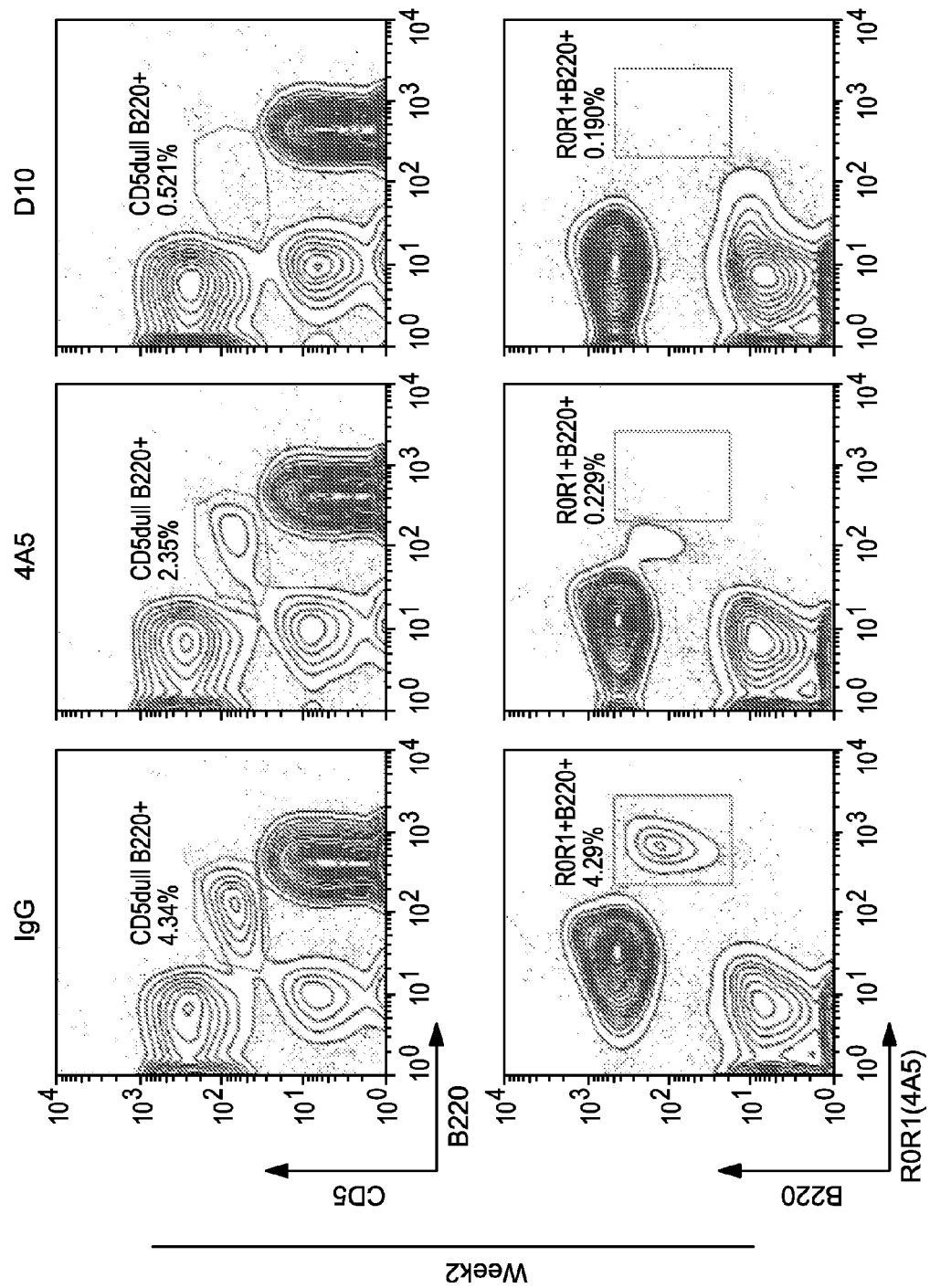

FIG. 3 is a series of graphs illustrating the results of a flow cytometric analysis which demonstrate that anti-ROR1 antibodies of the invention inhibited the development of CLL-like leukemia in ROR1 Tg mice. 2 weeks after adoptive transfer, the PBMC facs analysis were performed. The data showed the anti-ROR1 antibody D10 but not anti-ROR1 antibody 4A5 could markedly inhibit the $CD5^{dull}B220^+$ and $ROR1^{bright}B220^+$ leukemic B cell expansion.

Figure 4:
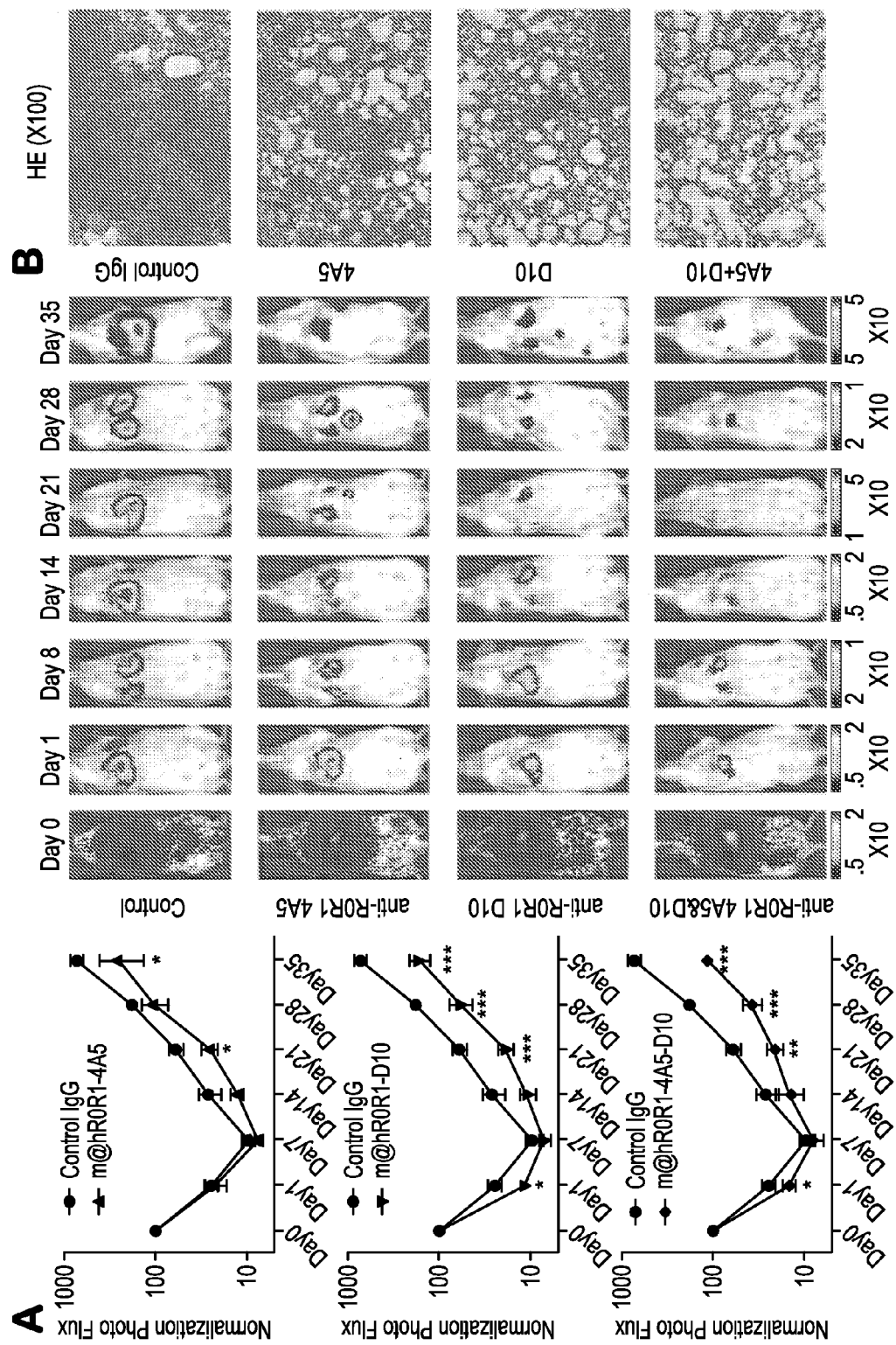

FIG. 4A is a series of graphs illustrating the results of in vivo testing in a murine model of human breast cancer. The anti-ROR1 antibodies inhibited breast cancer metastasis in rag-/-g-/- deficiency mice. 5E5 MDA-MB-231 breast cancer cell were transferred by i.v. injection to rag-/-g-/- mice on day 1. The rag-/-g-/- deficiency mice were also i.v. injected isotype control or anti-ROR1 antibody (4A5, D10, and 4A5 plus D10) on day 1, 3, 7 and 14 at 100 mg per mice. FIG. 4A (center) also provides images from IVIS in vivo imaging procedures on the above mice, which were performed every week. 5 weeks later, the mice were sacrificed and histology analysis were performed (FIG. 4B). The anti-ROR1 antibody D10 and the antibody combination (4A5 plus D10) both significantly inhibited metastasis of the breast cancer, with inhibition by D10 alone being greater than inhibition by 4a5 alone.

FIG. 5 provides a nucleotide coding sequence comparison of 4A5 Ig heavy chain (VH) to the closest germline mouse and human immunoglobulin (Ig) VH.

FIG. 6 provides a nucleotide coding sequence comparison of G6 Ig heavy chain (VH) to the closest germline mouse and human immunoglobulin (Ig) VH.

FIG. 7 provides a nucleotide coding sequence comparison of G3 Ig heavy chain (VH) to the closest germline mouse and human immunoglobulin (Ig) VH.

FIG. 8 provides a nucleotide coding sequence comparison of H10 Ig heavy chain (VH) to the closest germline mouse and human immunoglobulin (Ig) VH.

Figure 9:
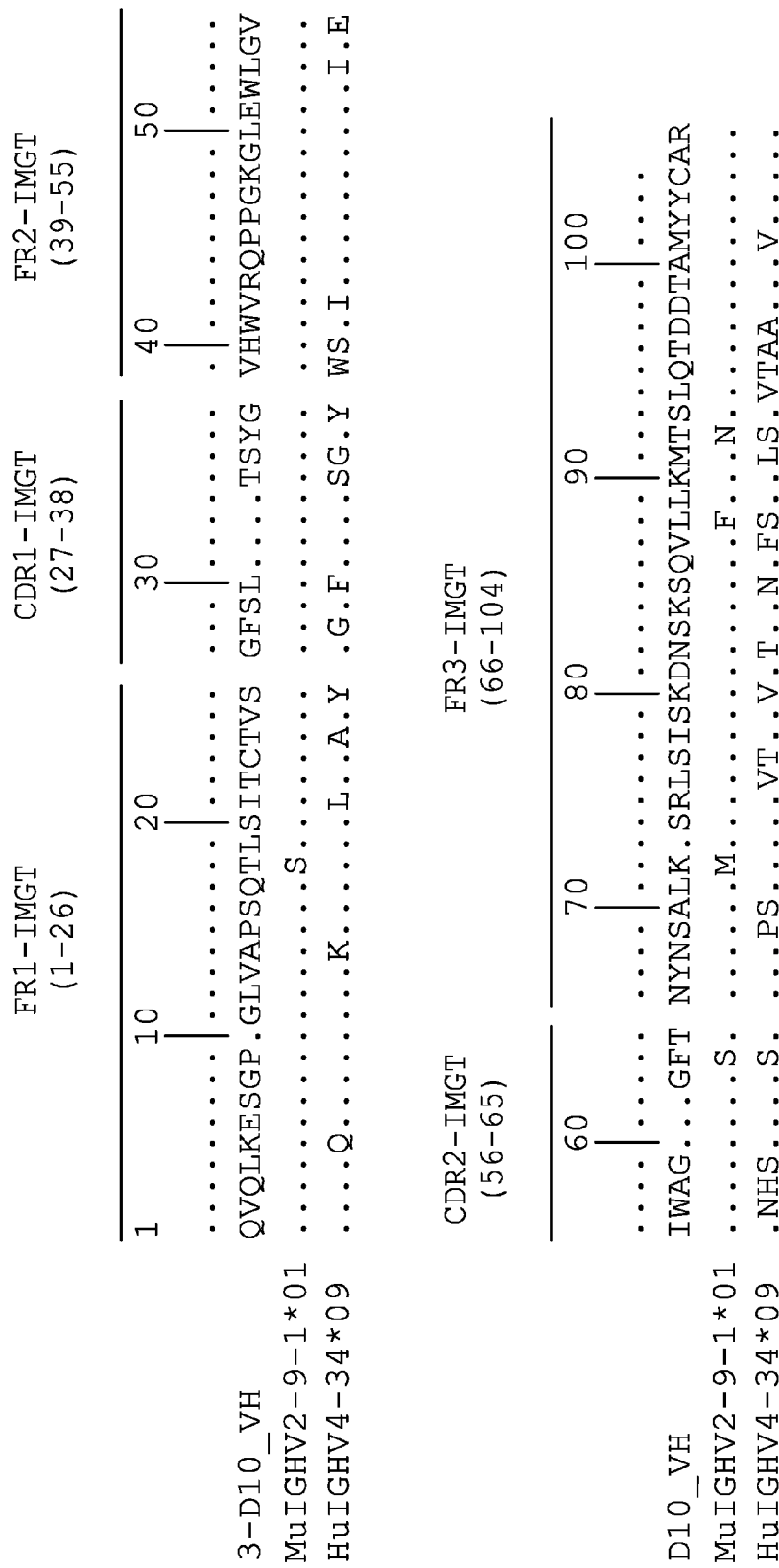

FIG. 9 provides a nucleotide coding sequence comparison of D10 Ig heavy chain (VH) to the closest germline mouse and human immunoglobulin (Ig) VH.

Figure 10:
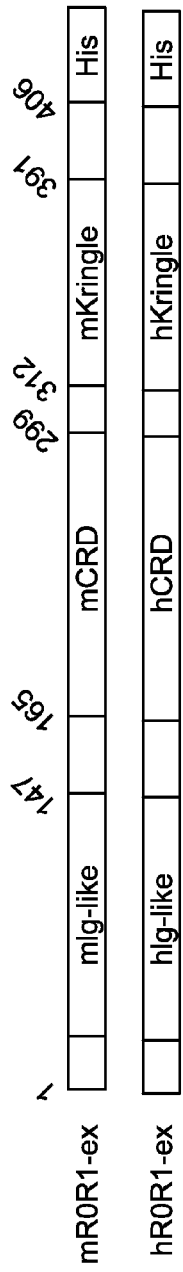

FIG. 10 is a diagram and chart depicting the highly conserved nature of human and murine ROR1.

FIG. 11 is a nucleotide comparison depicting the domain structure and sequence homology of human and murine ROR1 extracellular protein.

FIG. 12 is a chart indicating the extracellular domain which the anti-ROR1 mAbs bind the ROR1 protein.

Figure 13:
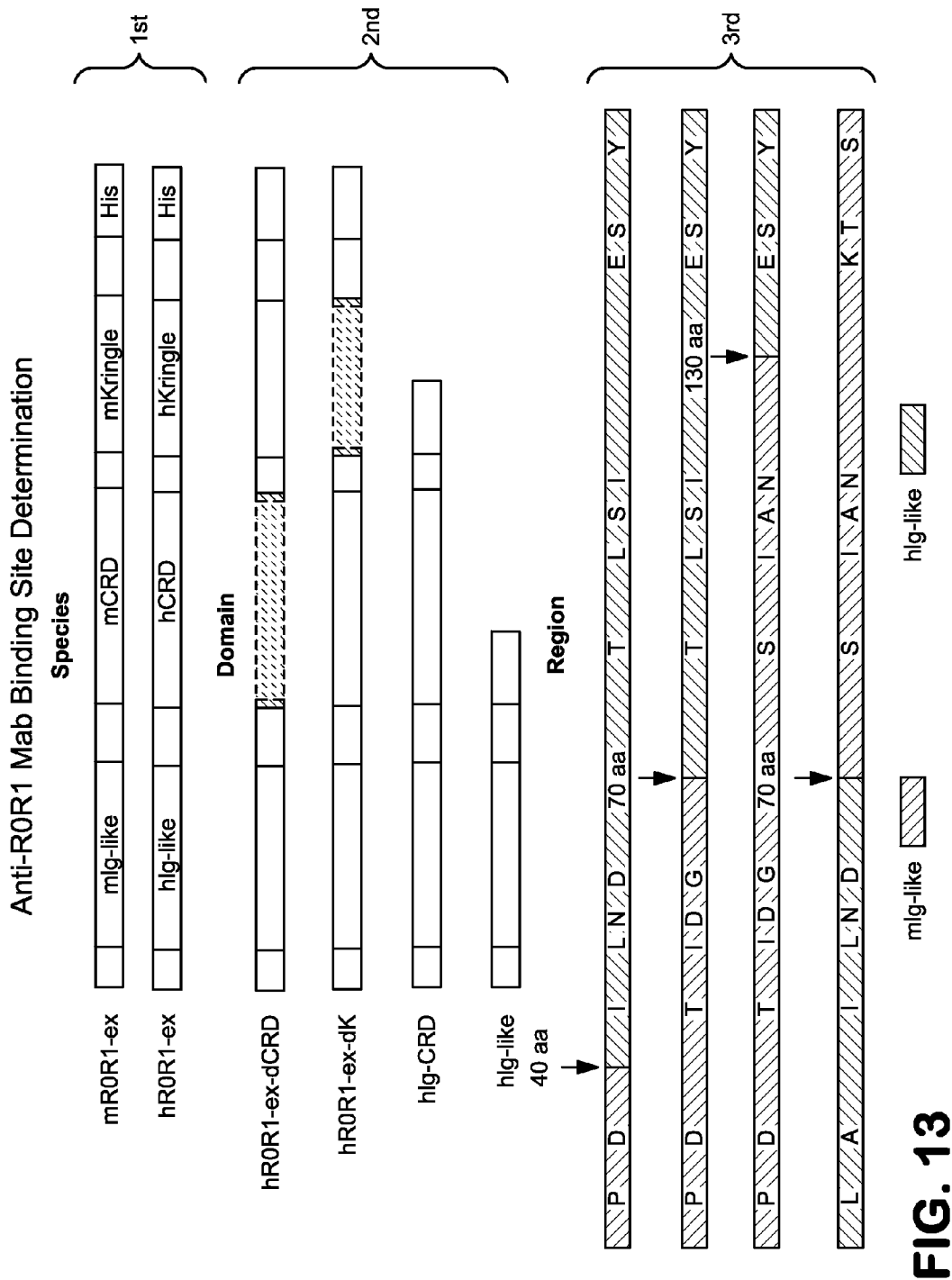

FIG. 13 is a diagram depicting the chimeric ROR1 proteins generated to determine the binding domain of each of the anti-ROR1 mAbs.

Figure 14:
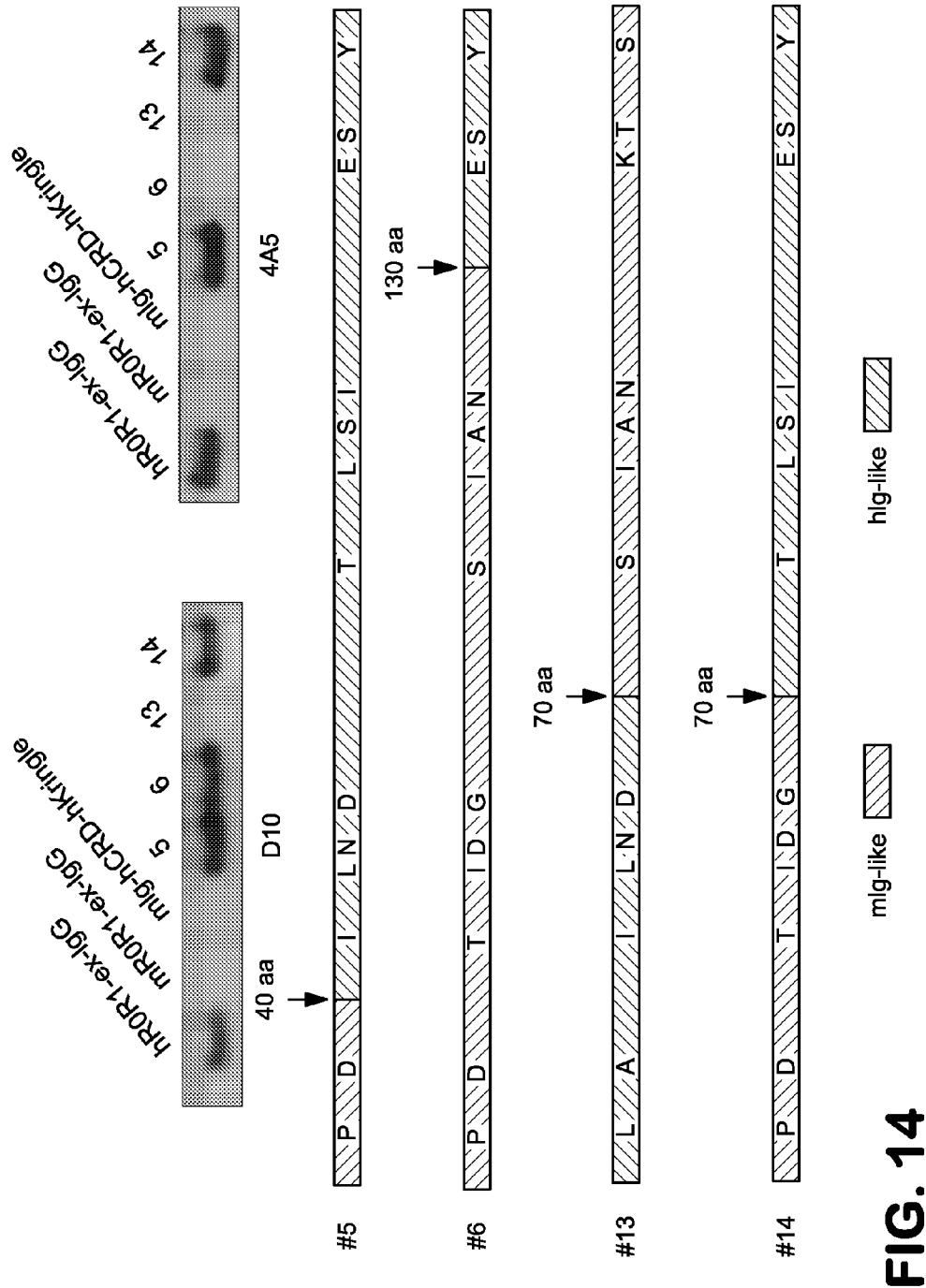

FIG. 14 is a diagram depicting the truncated ROR1 proteins generated to determine the sub-regions which each of the anti-ROR1 mAbs binds.

FIG. 15 is a diagram depicting the amino acids which were murinized to determine residues critical for mAb binding to human ROR1 and a western blot showing that the 138 glutamic acid residue is critical for antibody D10 binding to human ROR1.

FIG. 16 is a graph indicating the $K_D$ values for antibody D10 (FIG. 16a) and 4A5 (FIG. 16b).

FIG. 17 is a series of graphs illustrating the anti-ROR1 antibody D10 is highly active in in vivo assays.

Figure 18:
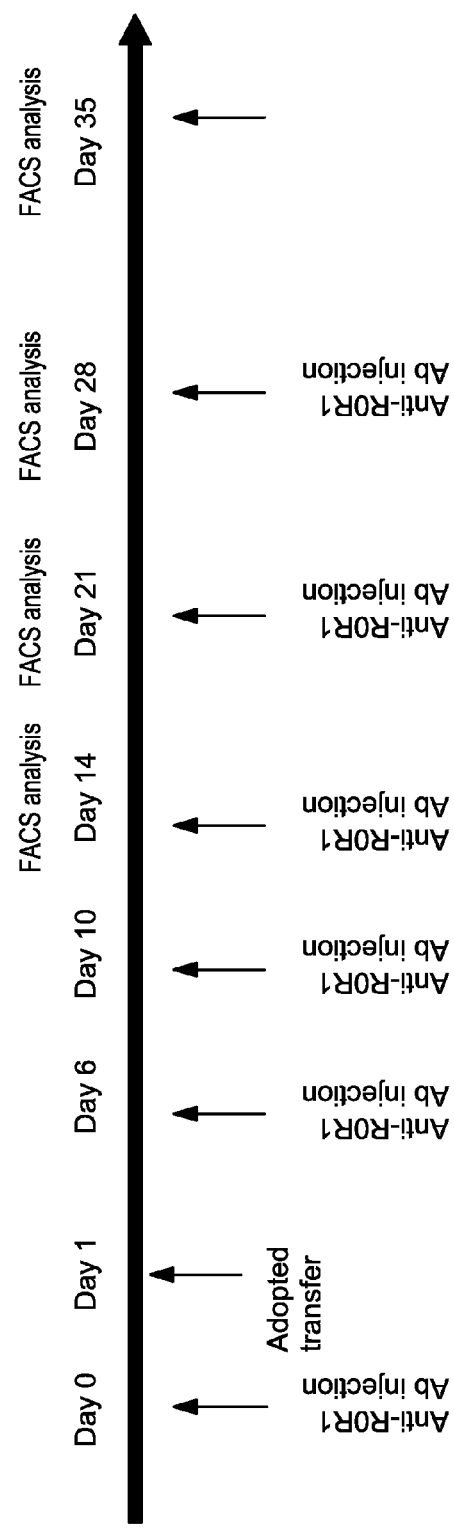

FIG. 18 is a diagram outlining the analysis of anti-ROR1 mAb on the adoptive transfer and engraftment of ROR1XTCL1 leukemic splenocytes. ROR1 Tg mice (5 mice/group) were given 250 ug of 4A5, D10 or control mIgG i.v. on day 0. The following day, $5\times10^5$ splenocytes from a ROR1 X TCL1 Tg mouse were adoptively transferred i.v. All mice were subsequently monitored weekly for expansion of $CD5^{dull}B200^+$ leukemic B cells by flow cytometery beginning at 2 weeks post transfer.

Figure 19:
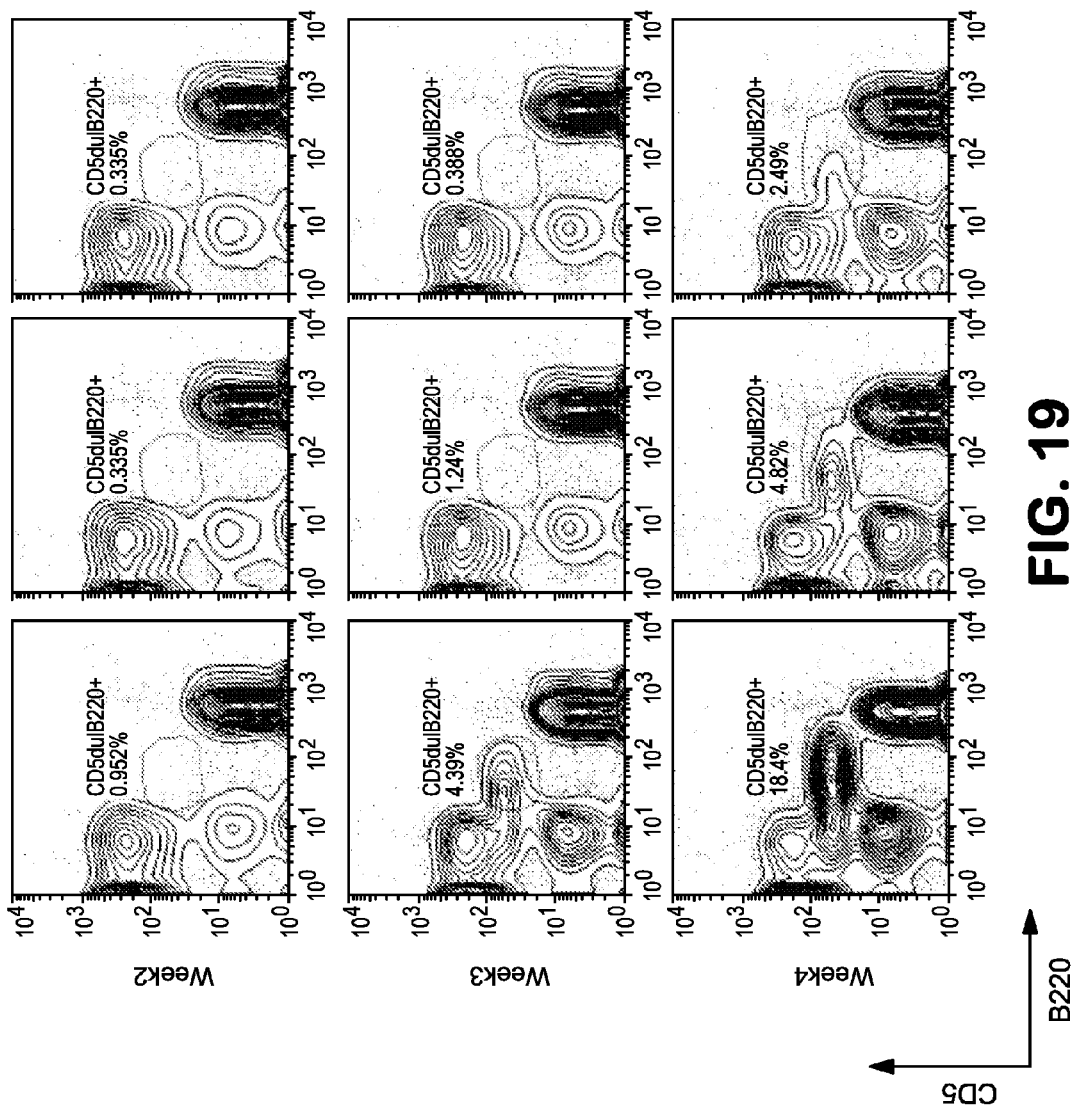

FIG. 19 a series of graphs illustrating the results of flow cytometric analysis of the anti-ROR1 antibodies inhibiting the development of CLL-like leukemia in ROR1 Tg mice. 2 weeks after adoptive transfer, the PBMC facs analysis were performed. The data showed the anti-ROR1 antibody D10 but not anti-ROR1 antibody 4A5 could markedly inhibit the $CD5^{dull}B220^+$ and $ROR1^{bright}B220^+$ leukemic B cell expansion.

Figure 20:
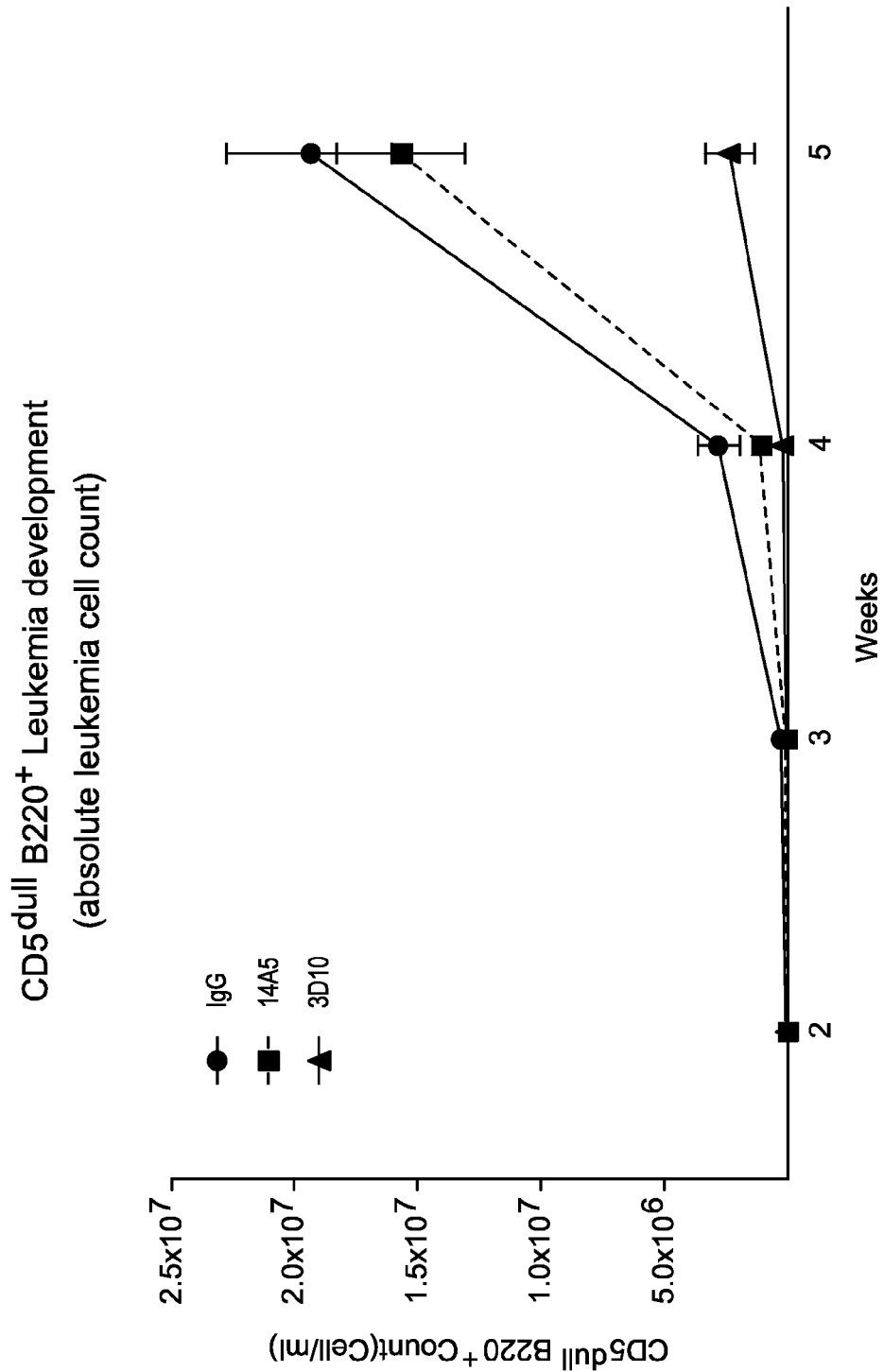

FIG. 20 is a graph illustrating that anti-ROR1 antibody D10 inhibits the development and expansion of ROR1xTCL1 leukemic B cells in the blood of recipient animals until two weeks after receiving the last infusion of the mAb.

Figure 21:
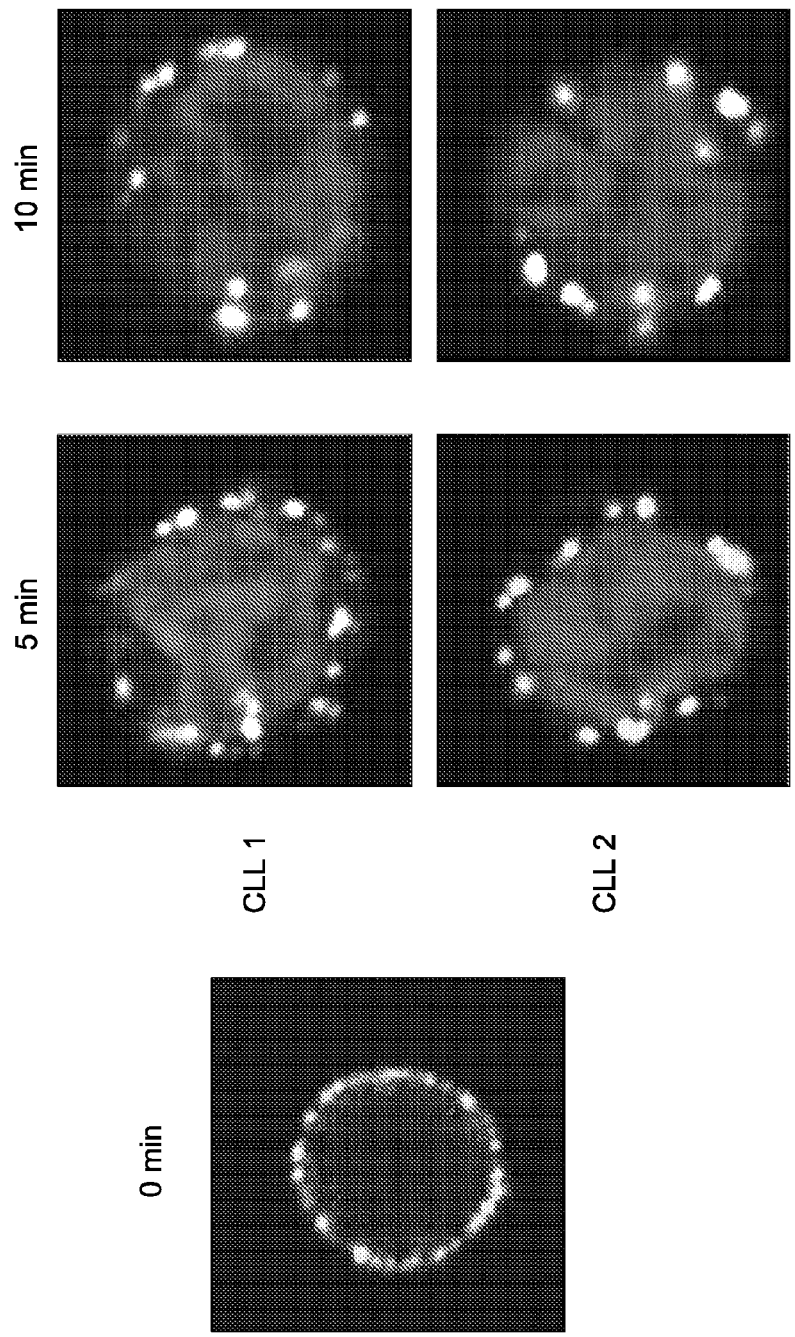

FIG. 21 is a depiction of the rapid internalization of the anti-ROR1 antibody D10 into CLL cells.

Figure 22:
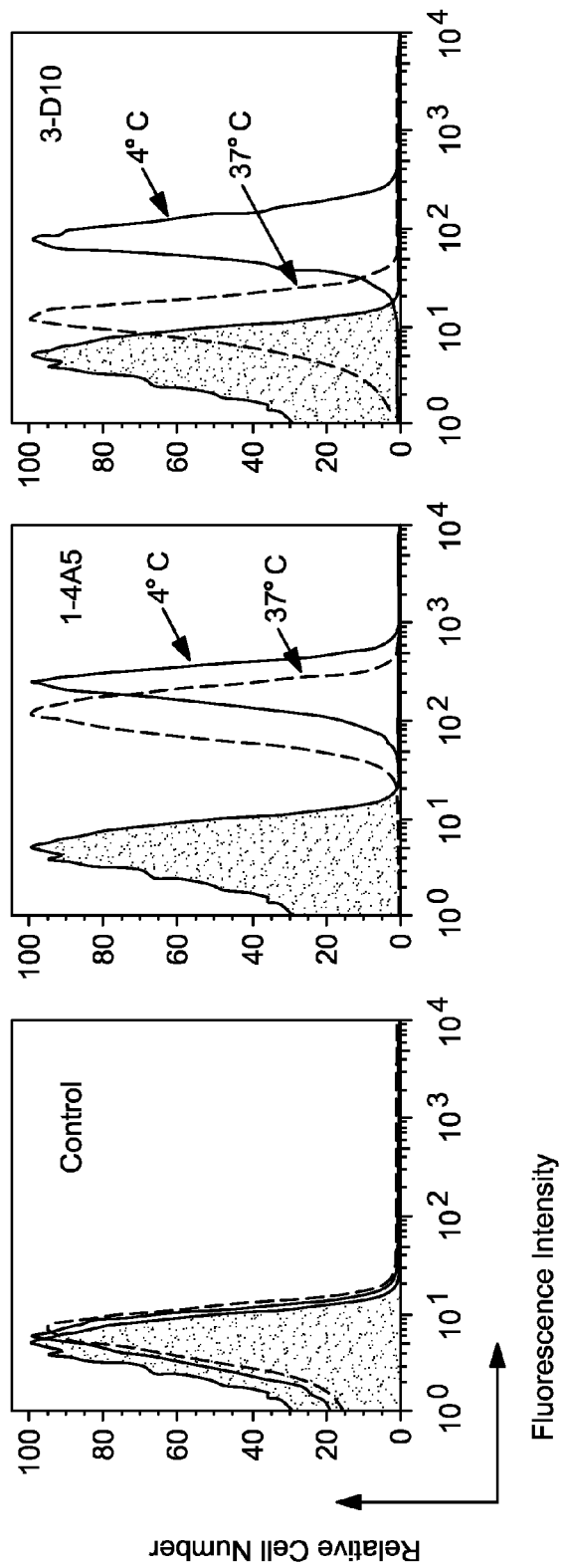

FIG. 22 is a series of graphs illustrating the results of flow cytometric analysis showing that anti-ROR1 antibodies D10 and 4A5 are both internalized into CLL cells. CLL cells were incubated with mouse anti-hROR1 Ab-Alex647 for 30 min at 4° C. Subsequently the cells were washed and either left at 4° C. or incubated for 4 hours at 37° C., followed by flow cytometry. The background signal with non-staining is also shown.

Figure 23:
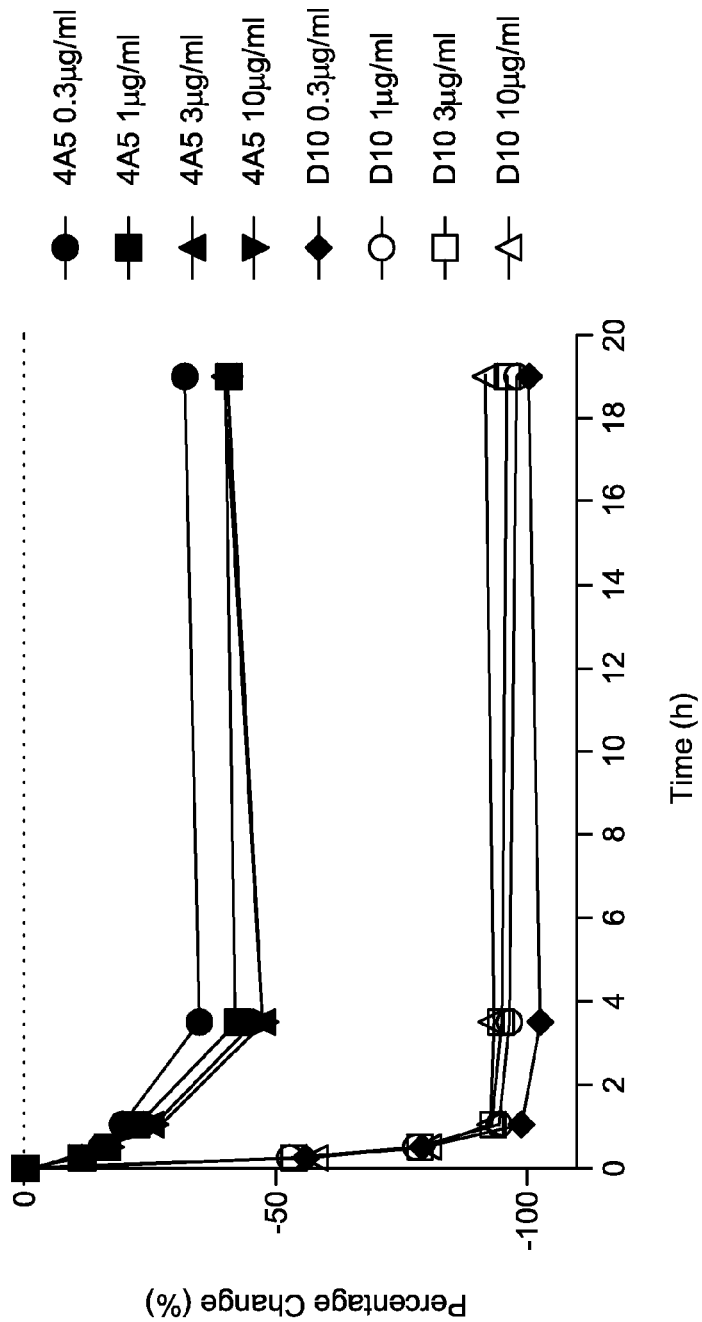

FIG. 23 is a graph illustrating the kinetics of the internalization of anti-ROR1 antibodies D10 and 4A5.

Figure 24:
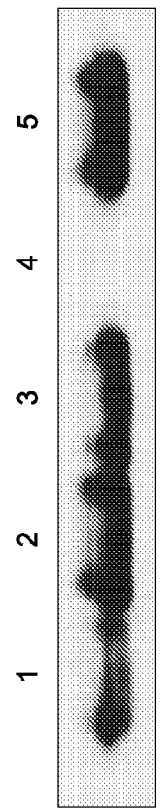

FIG. 24 is a diagram depicting the amino acids which were murinized to determine residues critical for mAb binding to human ROR1 and a western blot showing that the 111 isoleucine residue is critical for antibody 4A5 binding to human ROR1.

DETAILED DESCRIPTION OF THE PREFERRED EMBODIMENTS

The presently disclosed subject matter are described more fully below. However, the presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

Antibodies of the invention were produced monoclonally using techniques as previously described. Briefly, Naturally occurring antibodies are generally tetramers containing two light chains and two heavy chains. Experimentally, antibodies can be cleaved with the proteolytic enzyme papain, which causes each of the heavy chains to break, producing three separate subunits. The two units that consist of a light chain and a fragment of the heavy chain approximately equal in mass to the light chain are called the Fab fragments (i.e., the antigen binding fragments). The third unit, consisting of two equal segments of the heavy chain, is called the Fc fragment.

The Fc fragment is typically not involved in antigen-antibody binding, but is important in later processes involved in ridding the body of the antigen.

Because Fab and F(ab')$_2$ fragments are smaller than intact antibody molecules, more antigen-binding domains are available than when whole antibody molecules are used. Proteolytic cleavage of a typical IgG molecule with papain is known to produce two separate antigen binding fragments called Fab fragments which contain an intact light chain linked to an amino terminal portion of the contiguous heavy chain via by disulfide linkage. The remaining portion of the papain-digested immunoglobin molecule is known as the Fc fragment and consists of the carboxy terminal portions of the antibody left intact and linked together via disulfide bonds. If an antibody is digested with pepsin, a fragment known as an F(ab')$_2$ fragment is produced which lacks the Fc region but contains both antigen-binding domains held together by disulfide bonds between contiguous light and heavy chains (as Fab fragments) and also disulfide linkages between the remaining portions of the contiguous heavy chains (Handbook of Experimental Immunology. Vol 1: Immunochemistry, Weir, D. M., Editor, Blackwell Scientific Publications, Oxford (1986)).

As readily recognized by those of skill in the art, altered antibodies (e.g., chimeric, humanized, CDR-grafted, bifunctional, antibody polypeptide dimers (i.e., an association of two polypeptide chain components of an antibody, e.g., one arm of an antibody including a heavy chain and a light chain, or an Fab fragment including VL, VH, CL and CH antibody domains, or an Fv fragment comprising a VL domain and a VH domain), single chain antibodies (e.g., an scFv (i.e., single chain Fv) fragment including a VL domain linked to a VH domain by a linker, and the like) can also be produced by methods well known in the art.

Monoclonal antibody (mAb) technology can be used to obtain mAbs to ROR1. Briefly, hybridomas are produced using spleen cells from mice immunized with ROR1 antigens. The spleen cells of each immunized mouse are fused with mouse myeloma Sp 2/0 cells, for example using the polyethylene glycol fusion method of Galfre, G. and Milstein, C., Methods Enzymol., 73:3-46 (1981). Growth of hybridomas, selection in HAT medium, cloning and screening of clones against antigens are carried out using standard methodology (Galfre, G. and Milstein, C., Methods Enzymol., 73:3-46 (1981)):

HAT-selected clones are injected into mice to produce large quantities of mAb in ascites as described by Galfre, G. and Milstein, C., Methods Enzymol., 73:3-46 (1981), which can be purified using protein A column chromatography (Bio-Rad, Hercules, Calif.). mAbs are selected on the basis of their (a) specificity for ROR1, (b) high binding affinity, (c) isotype, and (d) stability.

mAbs can be screened or tested for ROR1 specificity using any of a variety of standard techniques, including Western Blotting (Koren, E. et al., Biochim. Biophys. Acta 876:91-100 (1986)) and enzyme-linked immunosorbent assay (ELISA) (Koren, E. et al., Biochim. Biophys. Acta 876:91-100 (1986)).

Humanized forms of mouse antibodies can be generated by linking the CDR regions of non-human antibodies to human constant regions by recombinant DNA techniques (see, e.g., Queen et al., Proc. Natl. Acad. Sci. USA 86:10029-10033, 1989 and WO 90/07861, each incorporated by reference). Human antibodies can be obtained using phage-display methods (see, e.g., Dower et al., WO 91/17271; McCafferty et al., WO 92/01047). In these methods, libraries of phage are produced in which members display different antibodies on their outer surfaces. Antibodies are usually displayed as Fv or Fab fragments. Phage displaying antibodies with a desired specificity may be selected by affinity enrichment.

Human antibodies may be selected by competitive binding experiments, or otherwise, to have the same epitope specificity as a particular mouse antibody. Using these techniques, a humanized ROR1 antibody having the human IgG1 constant region domain and the human kappa light chain constant region domain with the mouse heavy and light chain variable regions. The humanized antibody has the binding specificity of a mouse ROR1 mAb, specifically the 4A5 mAb described in Examples 4 and 5.

It may be desirable to produce and use functional fragments of a mAb for a particular application. The well-known basic structure of a typical IgG molecule is a symmetrical tetrameric Y-shaped molecule of approximately 150,000 to 200,000 daltons consisting of two identical light polypeptide chains (containing about 220 amino acids) and two identical heavy polypeptide chains (containing about 440 amino acids). Heavy chains are linked to one another through at least one disulfide bond. Each light chain is linked to a contiguous heavy chain by a disulfide linkage. An antigen-binding site or domain is located in each arm of the Y-shaped antibody molecule and is formed between the amino terminal regions of each pair of disulfide linked light and heavy chains. These amino terminal regions of the light and heavy chains consist of approximately their first 110 amino terminal amino acids and are known as the variable regions of the light and heavy chains. In addition, within the variable regions of the light and heavy chains there are hypervariable regions which contain stretches of amino acid sequences, known as complementarity determining regions (CDRs). CDRs are responsible for the antibody's specificity for one particular site on an antigen molecule called an epitope. Thus, the typical IgG molecule is divalent in that it can bind two antigen molecules because each antigen-binding site is able to bind the specific epitope of each antigen molecule. The carboxy terminal regions of light and heavy chains are similar or identical to those of other antibody molecules and are called constant regions. The amino acid sequence of the constant region of the heavy chains of a particular antibody defines what class of antibody it is, for example, IgG, IgD, IgE, IgA or IgM. Some classes of antibodies contain two or more identical antibodies associated with each other in multivalent antigen-binding arrangements.

Fab and F(ab')$_2$ fragments of mAbs that bind ROR1 can be used in place of whole mAbs. Because Fab and F(ab')$_2$ fragments are smaller than intact antibody molecules, more antigen-binding domains are available than when whole antibody molecules are used. Proteolytic cleavage of a typical IgG molecule with papain is known to produce two separate antigen binding fragments called Fab fragments which contain an intact light chain linked to an amino terminal portion of the contiguous heavy chain via by disulfide linkage. The remaining portion of the papain-digested immunoglobin molecule is known as the Fc fragment and consists of the carboxy terminal portions of the antibody left intact and linked together via disulfide bonds. If an antibody is digested with pepsin, a fragment known as an F(ab')$_2$ fragment is produced which lacks the Fc region but contains both antigen-binding domains held together by disulfide bonds between contiguous light and heavy chains (as Fab fragments) and also disulfide linkages between the remaining portions of the contiguous heavy chains (Handbook of Experimental Immunology. Vol 1: Immunochemistry, Weir, D. M., Editor, Blackwell Scientific Publications, Oxford (1986)).

With respect to particular antibodies, "specific binding" refers to antibody binding to a predetermined antigen. Typically, the antibody binds with an affinity corresponding to a $K_D$ of about $10^{-8}$ M or less, and binds to the predetermined antigen with an affinity (as expressed by $K_D$) that is at least 10 fold less, and preferably at least 100 fold less than its affinity for binding to a non-specific antigen (e.g., BSA, casein) other than the predetermined antigen or a closely-related antigen. Alternatively, the antibody can bind with an affinity corresponding to a $K_A$ of about $10^6$ $M^{-1}$, or about $10^7$ $M^{-1}$, or about $10^8 M^{-1}$, or $10^9$ $M^{-1}$ or higher, and binds to the predetermined antigen with an affinity (as expressed by $K_A$) that is at least 10 fold higher, and preferably at least 100 fold higher than its affinity for binding to a non-specific antigen (e.g., BSA, casein) other than the predetermined antigen or a closely-related antigen.

Also, reference to "an antibody having binding specificity for ROR-1 protein" includes antibody fragments having at least 90% or 95% sequence identity to any of the polypeptide sequences disclosed in SEQ ID NOs: 2. 4 6, 8, 12, 14, 16, 18 and 20, including variants modified by mutation to improve the utility thereof (e.g., improved ability to target specific cell types and the like). Such variants include those wherein one or more conservative substitutions are introduced into the heavy chain and/or the light chain of the antibody.

Such variants include those wherein one or more substitutions are introduced into the heavy chain nucleotide sequence and/or the light chain nucleotide sequence of the antibody. In some embodiments the variant has a light chain and/or heavy chain having a nucleotide sequence at least 80% or at least 90% or at least 95% identical to any of the nucleotide sequences set forth in SEQ ID NOs: 1, 3, 5, 7, 11, 13, 15, 17 and 19.

Polynucleotide sequences which code structural features of the antibodies of the invention include those whose sequences are set forth below. Each polynucleotide sequence is followed by the amino acid sequence of the encoded polypeptide. The light chain sequences which are considered to be "corresponding" to heavy chain sequences are those listed as being for the same antibody; i.e., the F2 heavy chain sequences correspond to the F2 light chain sequences, the D10 heavy chain sequences correspond to the D10 light chain sequences, and so forth.

SEQ ID NO: 1 4A5 Mouse Anti-ROR1 mAb Heavy Chain Variable Region Coding Sequence:

```
GAAGTGAAACTGGTGGAGTCTGGGGGAGGCTTAGTGAAGCCTGGAGGGTCCCTGAAACTCTC

CTGTGCAGCCTCTGGATT

CACTTTCAGTAGCTATGCCATGTCTTGGGTTCGCCAGATTCCAGAGAAGAGGCTGGAGTGGG

TCGCATCCATTAGTCGTG

GTGGTACCACCTACTATCCAGACAGTGTGAAGGGCCGATTCACCATCTCCAGAGATAATGTC

AGGAACATCCTGTACCTG

CAAATGAGCAGTCTGAGGTCTGAGGACACGGCCATGTATTACTGTGGAAGATATGATTACGA

CGGGTACTATGCAATGGA

CTACTGGGGTCAAGGAACCTCAGTCACCGTCTCCTCA
```

SEQ ID NO: 2 4A5 Mouse Anti-ROR1 mAb Heavy Chain Variable Region Polypeptide Sequence:

```
EVKLVESGGGLVKPGGSLKLSCAASGFTFSSYAMSWVRQIPEKRLEWVASISRGGTTYYPDS

VKGRFTISRDNVRNILYL

QMSSLRSEDTAMYYCGRYDYDGYYAMDYWGQGTSVTVSS
```

SEQ ID NO: 3 4A5 Mouse Anti-ROR1 mAb Light Chain Variable Region Coding Sequence:

```
GACATCAAGATGACCCAGTCTCCATCTTCCATGTATGCATCTCTAGGAGAGAGAGTCACTAT

CACTTGCAAGGCGAGTCC

GGACATTAATAGCTATTTAAGCTGGTTCCAGCAGAAACCAGGGAAATCTCCTAAGACCCTGA

TCTATCGTGCAAACAGAT

TGGTTGATGGGGTCCCATCAAGGTTCAGTGGCGGTGGATCTGGGCAAGATTATTCTCTCACC

ATCAACAGCCTGGAGTAT

GAAGATATGGGAATTTATTATTGTCTACAGTATGATGAATTTCCGTACACGTTCGGAGGGGG

GACCAAGCTGGAAATGAA

AC
```

SEQ ID NO: 4 4A5 Mouse Anti-ROR1 mAb Light Chain Variable Region Polypeptide Sequence:

DIKMTQSPSSMYASLGERVTITCKASPDINSYLSWFQQKPGKSPKTLIYRANRLVDGVPSRF

SGGGSGQDYSLTINSLEY

EDMGIYYCLQYDEFPYTFGGGTKLEMK

SEQ ID NO: 5 F2, F12 and G6 Mouse Anti-ROR1 mAb Heavy Chain Variable Region Coding Sequence:

GAGGTCCAGCTACAGCAGTCTGGACCTGAGCTGGAGAAGCCTGGCGCTTCAGTGAAGATATC

CTGCAAGGCTTCTGGTTT

CGCATTCACTGGCTACAACATGAACTGGGTGAAACAGACCAATGGAAAGAGCCTTGAGTGGA

TTGGAAGTATTGATCCTT

ACTATGGTGGTTCTACCTACAACCAGAAGTTCAAGGACAAGGCCACATTGACTGTAGACAAA

TCCTCCAGCACAGCCTAC

ATGCAACTCAAGAGCCTCACATCTGATGACTCTGCAGTCTATTACTGTGCAAGATCCCCGGG

GGGGGACTATGCTATGGA

CTACTGGGGTCAAGGAACCTCAGTCACCGTCTCCTCA

SEQ ID NO: 6 F2, F12 and G6 Mouse Anti-ROR1 mAb Heavy Chain Variable Region Polypeptide Sequence:

EVQLQQSGPELEKPGASVKISCKASGFAFTGYNMNWVKQTNGKSLEWIGSIDPYYGGSTYNQ

KFKDKATLTVDKSSSTAY

MQLKSLTSDDSAVYYCARSPGGDYAMDYWGQGTSVTVSS

SEQ ID NO: 7 F2, F12 and G6 Mouse Anti-ROR1 mAb Light Chain Variable Region Coding Sequence:

GACATCAAGATGACCCAGTCTCCATCTTCCATGTATGCATCTGTAGGAGAGAGAGTCACTAT

CACTTGTAAGGCGAGTCA

GGGCATTAATAGCTATTCAGGCTGGTTCCAGCAGAAACCAGGGAAATCTCCTAAGACCCTGA

TTTATCGTGGAAATAGAT

TGGTGGATGGGGTCCCATCAAGGTTCAGTGGCAGTGGATCTGGGCAAGATTATTCTCTCACC

ATCAGCAGCCTGGAGTAT

GAAGATATGGGAATTTATTATTGTCTACAGTATGATGAGTTTCCGTACACGTTCGGAGGGGG

GACCAAGCTGGAAATAAA

AC

SEQ ID NOs: 8 F2, F12 and G6 Mouse Anti-ROR1 mAb Light Chain Variable Region Polypeptide Sequence:

DIKMTQSPSSMYASVGERVTITCKASQGINSYSGWFQQKPGKSPKTLIYRGNRLVDGVPSRF

SGSGSGQDYSLTISSLEY

EDMGIYYCLQYDEFPYTFGGGTKLEIK

SEQ ID NO: 9 G3 Mouse Anti-ROR1 mAb Heavy Chain
Variable Region Coding Sequence:

CAGGTCCAACTGCAGCAGCCTGGGGCTGAGCTTGTGAAGCCTGGGACTTCAGTGAAGCTGTC

CTGCAAGGCTTCTGGCTA

CAACTTCACCAACTACTGGATAAACTGGGTGAAGCTGAGGCCTGGACAAGGCCTTGAGTGGA

TTGGAGAAATTTATCCTG

GTAGTGGTAGTACTAATTACAATGAGAAGTTCAAGAGCAAGGCCACACTGACTGCAGACACA

TCCTCCAGCACAGCCTAC

ATGCAACTCAGCAGCCTGGCATCTGAAGACTCTGCTCTCTATTACTGTGCAAGAGATGGTAA

CTACTATGCTATGGACTA

CTGGGGTCAAGGAACCTCAGTCACCGTCTCCTCA

SEQ ID NO: 10 G3 Mouse Anti-ROR1 mAb Heavy Chain
Variable Region Polypeptide Sequence:

QVQLQQPGAELVKPGTSVKLSCKASGYNFTNYWINWVKLRPGQGLEWIGEIYPGSGSTNYNE

KFKSKATLTADTSSSTAY

MQLSSLASEDSALYYCARDGNYYAMDYWGQGTSVTVSS

SEQ ID NO: 11 G3 Mouse Anti-ROR1 mAb Light Chain
Variable Region Coding Sequence:

GATATCCAGATGACACAGACTACATCCTCCCTGTCTGCCTCTCTGGGAGACAGAGTCACCAT

CACTTGCAGGGCAAGTCA

GGACATTAACAATTATTTAAACTGGTATCAACAGAAACCAGATGGAACTGTTAAACTCCTGA

TCTACTACACATCAGCAT

TACACTCAGGAGTCCCATCAAGGTTCAGTGGCAGTGGGTCTGGAACAGATTATTCTCTCACC

ATTAGCAACCTGGAACAA

GAAGATATTGCCACTTACTTTTGCCAACAGGGTAATACGCTTCCTCCGTACACGTTCGGAGG

GGGGACCAAGCTGGAAAT

AAAAC

SEQ ID NO: 12 G3 Mouse Anti-ROR1 mAb Light Chain
Variable Region Polypeptide Sequence:

DIQMTQTTSSLSASLGDRVTITCRASQDINNYLNWYQQKPDGTVKLLIYYTSALHSGVPSRF

SGSGSGTDYSLTISNLEQ

EDIATYFCQQGNTLPPYTFGGGTKLEIK

SEQ ID NO: 13 D10 Mouse Anti-ROR1 mAb Heavy Chain
Variable Region Coding Sequence:

CAGGTGCAGCTGAAGGAGTCAGGACCTGGCCTGGTGGCGCCCTCACAGACTCTGTCCATCAC

TTGCACTGTCTCTGGGTT

TTCATTAACCAGTTATGGTGTACACTGGGTTCGCCAGCCTCCAGGAAAGGGTCTGGAGTGGC

TGGGAGTAATATGGGCTG

-continued

GTGGATTCACAAATTATAATTCGGCTCTCAAGTCCAGACTGAGCATCAGCAAAGACAACTCC

AAGAGCCAAGTTCTCTTA

AAAATGACCAGTCTGCAAACTGATGACACAGCCATGTACTACTGTGCCAGGAGAGGTAGTTC

CTATTCTATGGACTATTG

GGGTCAAGGAACCTCAGTCACCGTCTCCTCA

SEQ ID NO: 14 D10 Mouse Anti-ROR1 mAb Heavy Chain
    Variable Region Polypeptide Sequence

QVQLKESGPGLVAPSQTLSITCTVSGFSLTSYGVHWVRQPPGKGLEWLGVIWAGGFTNYNSA

LKSRLSISKDNSKSQVLL

KMTSLQTDDTAMYYCARRGSSYSMDYWGQGTSVTVSS

SEQ ID NO: 15 D10 Mouse Anti-ROR1 mAb Light Chain
    Variable Region Coding Sequence:

GAAATTGTGCTCTCTCAGTCTCCAGCCATCACAGCTGCATCTCTGGGCCAAAAGGTCACCAT

CACCTGCAGTGCCAGTTC

AAATGTAAGTTACATCCACTGGTACCAGCAGAGGTCAGGCACCTCCCCCAGACCATGGATTT

ATGAAATATCCAAACTGG

CTTCTGGAGTCCCAGTTCGCTTCAGTGGCAGTGGGTCTGGGACCTCTTACTCTCTCACAATC

AGCAGCATGGAGGCTGAA

GATGCTGCCATTTATTATTGTCAGCAGTGGAATTATCCTCTTATCACGTTCGGCTCGGGGAC

AAAGTTGGAAATACAA

SEQ ID NO: 16 D10 Mouse Anti-ROR1 mAb Light Chain
    Variable Region Polypeptide Sequence:

EIVLSQSPAITAASLGQKVTITCSASSNVSYIHWYQQRSGTSPRPWIYEISKLASGVPVRFS

GSGSGTSYSLTISSMEAE

DAAIYYCQQWNYPLITFGSGTKLEIQ

SEQ ID NO: 17 H10 and G11 Mouse Anti-ROR1 mAb Heavy
    Chain Variable Region Coding Sequence:

GAAGTGAAGCTGGTGGAGTCTGGGGGAGGCTTAGTGAAGCCTGGAGGGTCCCTGAAACTCTC

CTGTGCAGCCTCTGGATT

CACTTTCAGTAGCTATGCCATGTCTTGGGTTCGCCAGACTCCAGAGAAGAGGCTGGAGTGGG

TCGCTTCCATTAGTACTG

GTGCTAGCGCCTACTTTCCAGACAGTGTGAAGGGCCGATTCACCATCTCCAGAGATAATGCC

AGGAACATCCTGTACCTG

CAAATGAGCAGTCTGAGGTCTGAGGACACGGCCATGTATTATTGTGCAAGGATTACTACGTC

TACCTGGTACTTCGATGT

CTGGGGCGCAGGGACCACGGTCACCGTCTCCTCA

SEQ ID NO: 18 H10 and G11 Mouse Anti-ROR1 mAb Heavy
Chain Variable Region Polypeptide Sequence:

EVKLVESGGGLVKPGGSLKLSCAASGFTFSSYAMSWVRQTPEKRLEWVASISTGASAYFPDS

VKGRFTISRDNARNILYL

QMSSLRSEDTAMYYCARITTSTWYFDVWGAGTTVTVSS

SEQ ID NO: 19 H10 and G11 Mouse Anti-ROR1 mAb Light
Chain Variable Region Coding Sequence:

GACATCAAGATGACCCAGTCTCCATCTTCCATGTATGCATCTCTAGGAGAGAGTCACTAT

CACTTGCAAGGCGAGTCA

GGACATTAATAGTTATTTAAGCTGGTTCCAGCAGAAACCAGGGAAATCTCCTAAGACCCTGA

TCTATCGTGCAAACAGAT

TGGTAGATGGGGTCCCATCAAGGTTCAGTGGCAGTGGATCTGGGCAAGATTATTCTCTCACC

ATCAGCAGCCTGGAGTAT

GAAGATATGGGAATTTATTATTGTCTACAGTATGATGAGTTTCCGTACACGTTCGGAGGGGG

GACCAAGCTGGAAATAAA

AC

SEQ ID NO: 20 H10 and G11 Mouse Anti-ROR1 mAb Light
Chain Variable Region Polypeptide Sequence:

DIKMTQSPSSMYASLGERVTITCKASQDINSYLSWFQQKPGKSPKTLIYRANRLVDGVPSRF

SGSGSGQDYSLTISSLEY

EDMGIYYCLQYDEFPYTFGGGTKLEIK

In one aspect, antibodies are provided in which a heavy chain encoded by the polynucleotide sequence of SEQ ID NO:13 and a light chain encoded by the polynucleotide sequence of SEQ ID NO:15.

In another aspect, an antibody of the present invention contains a heavy chain encoded by the polynucleotide sequence of SEQ ID NO:1 and a light chain encoded by the polynucleotide sequence of SEQ ID NO:3.

In further aspects, antibodies are provided which have a heavy chain encoded by the polynucleotide sequence of SEQ ID NO: 5 and a light chain encoded by the polynucleotide sequence of SEQ ID NO: 7; or by the polynucleotide sequence of SEQ ID NO: 9 and a light chain encoded by the polynucleotide sequence of SEQ ID NO: 11; or by the polynucleotide sequence of SEQ ID NO: 15 and a light chain encoded by the polynucleotide sequence of SEQ ID NO: 17.

In another aspect, antibodies are provided which contain a heavy chain with the polypepetide sequence of SEQ ID NO:14 and a light chain with the polypeptide sequence of SEQ ID NO:16.

In another aspect, antibodies are provided which contain a heavy chain with the polypeptide sequence of SEQ ID NO:2 and a light chain with the polypeptide sequence of SEQ ID NO:4.

In one embodiment, isolated polynucleotides which encode an antibody that specifically binds ROR1 protein are provided which are (a) comprised of a heavy chain region coded by polynucleotides having at least 90% sequence identity with any of the sequences selected from the group consisting of SEQ ID NOs: 1, 5, 9, 13 or 17, (b) comprised of a corresponding light chain region encoded by polynucleotides having at least 90% sequence identity with any of the sequences selected from the group consisting of SEQ ID NOs: 3, 7, 11, 15 or 19, and (c) specifically binds either the 3' end or middle portion of the Ig-like region of the extracellular domain of human or murine ROR-1 protein.

Also provided are antibodies which bind residues within the middle of the Ig-like region of the extracellular domain of human or murine ROR-1 protein (amino acids 1-147 in the human molecule). In one aspect, the antibodies of the present invention bind to amino acids 70-130 of human ROR1. Examples of such antibodies include 4A5, G11, H10 and G3.

Alternatively or additionally, a residue corresponding to the one found in the extracellular domain of human ROR-1 protein at position 111 is critical to the binding activity of the antibodies.

Further provided are antibodies that bind residues within the 3' Ig-like region and the linker region between the Ig-like domain and the CRD domain of human or murine ROR-1 protein (amino acids 1-165 in the human molecule). In one aspect, the antibodies of the present invention bind to amino acids 130-165 of human ROR1. Examples of such antibodies include D10, F2, F12 and G6.

Alternatively or additionally, the antibodies bind a glutamic acid residue corresponding to the one found in the extracellular domain of human ROR-1 protein at position 138.

Alternatively or additionally, a residue corresponding to the one found in the extracellular domain of human ROR-1 protein at position 138 is critical to the binding activity of the antibodies.

Alternatively or additionally, the encoded antibody has in vivo activity in reducing leukemic or lymphomic cell burden in an art-accepted animal model at a rate of 2-8 times, or at least 2, 3, 4, 5, 6, 7, or 8 times, that of wild-type human anti-ROR1 antibody or monoclonal 4A5 antibody (disclosed herein).

Alternatively or additionally, the encoded antibody has in vivo activity in inhibiting $CD5^{dull}B220^+$ and $ROR1^{bright}B220^+$ leukemic B cell expansion.

Alternatively or additionally, the encoded antibody is internalized into leukemic or lymphomic cells at a rate of at least 2 times, or at least 2, 3, 4, 5, 6, 7, 8, 9 or 10 times that of monoclonal antibody 4A5. Such antibodies are particularly useful as carriers for drug delivery into a targeted cell.

An example of an antibody possessing all of the aforementioned functional characteristics is D10, which has a heavy chain region encoded by SEQ ID NO: 13 and a light chain region encoded by SEQ ID NO: 15.

In another aspect, polypeptides are provided which consist of or comprise antibodies which specifically bind ROR1 protein and are (a) comprised of a heavy chain region having at least 90% sequence identity with any of the sequences of SEQ. ID. NOs: 2, 6, 10, 14 or 18, (b) comprised of a corresponding light chain region having at least 90% sequence identity with any of the sequences of SEQ ID NOs: 4, 8, 12, 16 or 20, and (c) specifically binds either the 3' end or middle portion of the Ig-like region of the extracellular domain of human or murine ROR-1 protein. In one aspect, the isolated polypeptide is an antibody. In a further aspect, the polypeptide is a Fab or F(ab)'2.

In certain embodiments, an antibody of the present invention may further contain a detectable label. Such labels are known in the art and include radio-isotopes and fluorescent labels. As such, internalization of a compound evidencing passage through transporters can be detected by detecting a signal from within a cell from any of a variety of reporters. The reporter can be a label such as a fluorophore, a chromophore, a radioisotope. Confocal imagining can also be used to detect internalization of a label as it provides sufficient spatial resolution to distinguish between fluorescence on a cell surface and fluorescence within a cell; alternatively, confocal imaging can be used to track the movement of compounds over time. In another approach, internalization of a compound is detected using a reporter that is a substrate for an enzyme expressed within a cell. Once the complex is internalized, the substrate is metabolized by the enzyme and generates an optical signal or radioactive decay that is indicative of uptake. Light emission can be monitored by commercial PMT-based instruments or by CCD-based imaging systems. In addition, assay methods utilizing LCMS detection of the transported compounds or electrophysiological signals indicative of transport activity are also employed.

In certain therapeutic embodiments, the selected antibody may be administered alone, in combination with another antibody of the invention, or with one or more combinatorial therapeutic agents to treat an ROR-1 cancer. When one or more the antibodies described herein are administered as therapeutic agents, they may exert a beneficial effect in the subject by a variety of mechanisms. For example, in certain embodiments, antibodies that specifically bind ROR1 are purified and administered to a patient to neutralize one or more forms of ROR1, to block one or more activities of ROR1, or to block or inhibit an interaction of one or more forms of ROR1 with another biomolecule; e.g., to treat CLL or other ROR1 cancers. All such therapeutic methods are practiced by delivery of a therapeutically effective dosage of a pharmaceutical composition containing the therapeutic antibodies and agents, which can be determined by a pharmacologist or clinician of ordinary skill in human cancer immunotherapy.

In one embodiment, the present invention provides for a method for of treating cancer by the administration to a human subject in need thereof of a therapeutically effective dose of an antibody according to the invention.

In another embodiment, the present invention provides a method for of treating cancer comprising administration to a human subject in need thereof of a therapeutically effective dose of an antibody according to the invention.

Advantageously, the methods of the invention provide for reduction of leukemic or lymphomic cell burden (as demonstrated in and equivalent to an art-accepted animal model) of 2-8 times, or at least 2, 3, 4, 5, 6, 7, or 8 times, that of wild-type human anti-ROR1 antibody or monoclonal 4A5 antibody (disclosed herein).

The methods of the invention further provide a therapeutic approach to inhibiting $CD5^{dull}B220^+$ and $ROR1^{bright}B220^+$ leukemic B cell expansion.

As discussed herein, the antibodies of the invention may include humanized antibodies, and can be combined for therapeutic use with additional active or inert ingredients, e.g., in conventional pharmaceutically acceptable carriers or diluents, e.g., immunogenic adjuvants, and optionally with adjunctive or combinatorially active molecules such as antiinflammatory and anti-fibrinolytic drugs. Antibodies which readily internalize into cells as demonstrated herein with respect to the D10 antibody are also of particular use as carriers for drug delivery into target cells (for example, as shown in FIGS. 21-23). Those of ordinary skill in the art will be familiar with methods for producing antibody-drug conjugates useful in such drug delivery protocols.

In carrying out various assay, diagnostic, and therapeutic methods of the invention, it is desirable to prepare in advance kits comprises a combination of antibodies as described herein with other materials. For example, in the case of sandwich enzyme immunoassays, kits of the invention may contain an antibody that specifically binds ROR1 optionally linked to an appropriate carrier, a freeze-dried preparation or a solution of an enzyme-labeled monoclonal antibody which can bind to the same antigen together with the monoclonal antibody or of a polyclonal antibody labeled with the enzyme in the same manner, a standard solution of purified ROR1, a buffer solution, a washing solution, pipettes, a reaction container and the like. In addition, the kits optionally include labeling and/or instructional materials providing directions (i.e., protocols) for the practice of the methods described herein in an assay environment. While the instructional materials typically comprise written or printed materials, they are not limited to such. Any medium capable of storing such instructions and communicating them to an end user is contemplated. Such media include, but are not limited to electronic storage media (e.g., magnetic discs, tapes, cartridges, chips), optical media (e.g., CD ROM), and the like. Such media may include addresses to internet sites that provide such instructional materials.

In general, an in vitro method of diagnosing a ROR-1 cancer will comprise contacting putative cancer cells from a human subject with an antibody according to the invention, and detecting binding with ROR-1 expressed on said cells as compared to expression on post-embryonic human non-cancer cells. All such diagnostic methods are practiced by delivery of a diagnostically effect quantity of antibodies according to the invention, which can be determined by a diagnostician or in vitro diagnostic engineer of ordinary skill in human cancer diagnosis.

The following examples are intended to illustrate but not limit the invention.

EXAMPLE 1

Generation of Monoclonal Anti-ROR1 Antibodies

For the production of the hybridoma-generated mAbs, mice were inoculated with DNA, protein and adenoviral constructs that express the extracellular portion (AA 1-406) of the ROR1 protein that include the Ig-like, CRD and Kringle domains and adjacent linker regions (FIGS. 10-11). Because of the high degree of homology between the murine and human molecules, a variety of cytokines and immune stimulatory agents, such as Freund's Complete Adjuvant, were co-injected to maximize the generation of anti-human ROR1 antibodies. Hybridoma-generated mAbs were generated and screened for binding to human and murine ROR1. An example of hybridoma derived mAbs is D10.

EXAMPLE 2

Generation of Anti-ROR1 Antibodies Using Phage Display

A second set of antibodies was generated through the use of a proprietary enhanced phage library (Alere, Inc. San Diego). These anti-human ROR1 antibodies bind epitopes that span the entire length of the extra-cellular domain of the ROR1 protein (FIG. 12). An example of a phage display derived anti-ROR1 antibody is 4A5.

EXAMPLE 3

In Vitro Analysis of Anti-ROR1 Antibodies

Antibodies generated through either hybridomas or phage display were screened for binding to human and murine ROR1. It was determined that the anti-ROR1 antibodies D10 and 4A5 bound only to human ROR1 and did not cross react with murine ROR1.

EXAMPLE 4

Determination of Binding Sites for Anti-ROR1 Antibodies

Because the anti-ROR1 mAbs are species specific, a series of chimeric proteins were generated that were used to determine the binding site for each of the anti-ROR1 mAbs (FIG. 13). As a second level screen, a series of deletion constructs were generated to determine the actual extracellular ROR1 domain to which the mAbs bind. Once the binding domain was identified, truncated chimeric ROR1 molecules to identify specific sub-regions were generated that are recognized by the anti-human ROR1 mAbs (FIG. 14). As a final step, the actual amino acids targeted by these antibodies were determined. For this final screen, murinized human amino acids in the sub-domain fragments were generated to determine critical residues required for mAb binding (FIG. 15). From this screening paradigm, the binding sub-domains for the mAbs were determined (FIG. 15). It was determine that the D10 anti-human ROR1 mAb required the glutamic acid residue at position 138 for binding to the Ig-like domain of the human ROR1 molecule. When this amino acid is replaced with the murine molecule's lysine residue, the D10 molecule no longer bound to the ROR1 protein.

In a similar manner, it was determined that 4A5 anti-human ROR1 mAb required the isoleucine residue at position 111 for binding to human ROR1 molecule (FIG. 24). When this amino acid is replaced with the murine molecule's asparagine residue, the 4A5 molecule no longer bound to the ROR1 protein. It was also determined that the anti-ROR1 antibodies G11, H10 and G3 bind the same region as 4A5.

Using standard cross blocking techniques the binding sites for anti-ROR1 antibodies F2, F12 and G6 were determined. These experiments determined that antibodies F2, F12 and G6 cross block the anti-ROR1 antibody D10, indicating that they share a binding site.

EXAMPLE 5

Determination of the $K_D$ Values for the Anti-ROR1 Antibodies D10 and 4A5

The $K_D$ values for the anti-ROR1 antibodies was determined using standard techniques. It was determined that the $K_D$ for the D10 antibody was 40 nM and for the antibody 4A5 was 4 nM (FIGS. 16A & B).

EXAMPLE 6

In Vivo Analysis of Anti-ROR1 Antibodies

The D10 mAb was assessed in several in vivo models. In a murine in vivo xenograph, niche-dependent, activity model two doses of the mAb were administered at 10 mg/kg against 4 primary patient CLL cells in 76 mice. As shown in FIG. 17, D10 mAb substantially eliminated patient CLL cells in a dose dependent manner. In contrast, the 4A5 mAb had minimal activity in these studies even though the kDa of this mAb is 10 fold greater (4 vs. 40) for the D10 mAb.

In addition to this activity model, the D10 mAb was also tested in an immune competent transgenic mouse model that spontaneously generates leukemic cells expressing the human ROR1 protein (FIGS. 18-20). The ROR1-specific mAbs D10 and 4A5 or control IgG antibodies (10 mg/kg) were administered before and after adoptive transfer of ROR1xTCL1 CLL B cells into Balb C mice. The D10 mAb, but not control IgG or 4A5, was able to inhibit the development and expansion of the ROR1xTCL1 leukemic B cells in the blood of recipient animals until two weeks after receiving the last infusion of MAb.

Along with the anti-leukemic activity of this mAb, it has also been shown that the D10 anti-ROR1 antibody is internalized into patient CLL cells and B cell leukemia and lymphoma cell lines at a greater rate and degree than other anti-ROR1 MAbs that bind other antigenic sites on the extracellular portion of the ROR1 protein (FIGS. 21-23). Because of the absence of the ROR1 protein on post-partum tissues and its rapid rate of internalization, the D10 mAb may serve as an excellent carrier protein for drugs; for example, for use in directed antibody-drug conjugate (ADC) mediated cytotoxicity. Based on these preclinical findings, the D10 mAb has potential to have therapeutic activity against ROR1 expressing leukemias, lymphomas and solid tumor cancers as a targeted therapy and/or conjugated drug carrier.

Although the foregoing subject matter has been described in some detail by way of illustration and example for purposes of clarity of understanding, it will be understood by those skilled in the art that certain changes and modifications can be practiced within the scope of the appended claims.

What is claimed is:

1. An isolated antibody that specifically binds receptor tyrosine kinase like orphan receptor one (ROR1) protein and comprises a heavy chain variable region comprising SEQ ID NO:14 and a light chain region comprising SEQ ID NO:16.

2. The antibody according to claim 1, wherein it further specifically binds either the 3' or middle Ig-like region of the extracellular domain of human or murine ROR-1 protein.

3. The antibody according to claim 1, wherein it binds the 3' end of the Ig-like region of the extracellular domain of human or murine ROR-1 protein from position 1-147.

4. The antibody according to claim 3, wherein it further binds a glutamic acid residue corresponding to the one found in the extracellular domain of human ROR-1 protein at position 138.

5. The antibody according to claim 1, wherein it further reduces leukemic or lymphomic cell burden in an art-accepted animal model at a rate of 2-8 times, or at least 2, 3, 4, 5, 6, 7, or 8 times that of wild-type human anti-ROR1 antibody or monoclonal 4A5 antibody.

6. The antibody according to claim 1, wherein it further inhibits $CD5^{dull}$ $B220^+$ and $ROR1^{bright}$ $B220^+$ leukemic B cell expansion.

7. The antibody according to claim 1, wherein it further is internalized into leukemic or lymphomic cells at a rate of at least 2 times, or at least 2, 3, 4, 5, 6, 7, 8, 9 or 10 times that of monoclonal antibody 4A5.

8. A pharmaceutically acceptable anti-ROR1 antibody composition comprising the antibody according to claim 1 and a pharmaceutically acceptable carrier.

9. An isolated antibody which binds the same epitope as antibody D10, wherein the heavy chain variable region of D10 is encoded by SEQ ID NO:13 and the light chain variable region of D10 is encoded by SEQ ID NO:15.

* * * * *

SEQUENCE LISTING

<160> NUMBER OF SEQ ID NOS: 37

<210> SEQ ID NO 1
<211> LENGTH: 357
<212> TYPE: DNA
<213> ORGANISM: Mouse

<400> SEQUENCE: 1
gaagtgaaac tggtggagtc tgggggaggc ttagtgaagc ctggagggtc cctgaaactc     60
tcctgtgcag cctctggatt cactttcagt agctatgcca tgtcttgggt tcgccagatt    120
ccagagaaga ggctggagtg ggtcgcatcc attagtcgtg gtggtaccac ctactatcca    180
gacagtgtga agggccgatt caccatctcc agagataatg tcaggaacat cctgtacctg    240
caaatgagca gtctgaggtc tgaggacacg gccatgtatt actgtggaag atatgattac    300
gacgggtact atgcaatgga ctactgggt caaggaacct cagtcaccgt ctcctca       357

<210> SEQ ID NO 2
<211> LENGTH: 119
<212> TYPE: PRT
<213> ORGANISM: Mouse

<400> SEQUENCE: 2

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Ile Pro Glu Lys Arg Leu Glu Trp Val
        35                  40                  45

Ala Ser Ile Ser Arg Gly Gly Thr Thr Tyr Tyr Pro Asp Ser Val Lys
    50                  55                  60

Gly Arg Phe Thr Ile Ser Arg Asp Asn Val Arg Asn Ile Leu Tyr Leu
65                  70                  75                  80

Gln Met Ser Ser Leu Arg Ser Glu Asp Thr Ala Met Tyr Tyr Cys Gly
                85                  90                  95

Arg Tyr Asp Tyr Asp Gly Tyr Tyr Ala Met Asp Tyr Trp Gly Gln Gly
            100                 105                 110

Thr Ser Val Thr Val Ser Ser
        115

<210> SEQ ID NO 3
<211> LENGTH: 322
<212> TYPE: DNA
<213> ORGANISM: Mouse

<400> SEQUENCE: 3
gacatcaaga tgacccagtc tccatcttcc atgtatgcat ctctaggaga gagagtcact     60
atcacttgca aggcgagtcc ggacattaat agctatttaa gctggttcca gcagaaacca    120
gggaaatctc ctaagaccct gatctatcgt gcaaacagat tggttgatgg ggtcccatca    180
aggttcagtg gcggtggatc tgggcaagat tattctctca ccatcaacag cctggagtat    240
gaagatatgg gaatttatta ttgtctacag tatgatgaat tccgtacac gttcggaggg    300 gggaccaagc tggaaatgaa ac                                             322

<210> SEQ ID NO 4
<211> LENGTH: 107
<212> TYPE: PRT
<213> ORGANISM: Mouse

<400> SEQUENCE: 4

Asp Ile Lys Met Thr Gln Ser Pro Ser Ser Met Tyr Ala Ser Leu Gly
1               5                   10                  15

Glu Arg Val Thr Ile Thr Cys Lys Ala Ser Pro Asp Ile Asn Ser Tyr
            20                  25                  30

Leu Ser Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
50                  55                  60

Gly Gly Ser Gly Gln Asp Tyr Ser Leu Thr Ile Asn Ser Leu Glu Tyr
65                  70                  75                  80

Glu Asp Met Gly Ile Tyr Tyr Cys Leu Gln Tyr Asp Glu Phe Pro Tyr
                85                  90                  95

Thr Phe Gly Gly Gly Thr Lys Leu Glu Met Lys
            100                 105

<210> SEQ ID NO 5
<211> LENGTH: 357
<212> TYPE: DNA
<213> ORGANISM: Mouse

<400> SEQUENCE: 5
gaggtccagc tacagcagtc tggacctgag ctggagaagc ctggcgcttc agtgaagata      60
tcctgcaagg cttctggttt cgcattcact ggctacaaca tgaactgggt gaaacagacc     120
aatggaaaga gccttgagtg gattggaagt attgatcctt actatggtgg ttctacctac     180
aaccagaagt tcaaggacaa ggccacattg actgtagaca atcctccag cacagcctac      240 atgcaactca gagcctcac atctgatgac tctgcagtct attactgtgc aagatccccg      300
gggggggact atgctatgga ctactgggt caaggaacct cagtcaccgt ctcctca        357

<210> SEQ ID NO 6
<211> LENGTH: 119
<212> TYPE: PRT
<213> ORGANISM: Mouse

<400> SEQUENCE: 6

Glu Val Gln Leu Gln Gln Ser Gly Pro Glu Leu Glu Lys Pro Gly Ala
1               5                   10                  15

Ser Val Lys Ile Ser Cys Lys Ala Ser Gly Phe Ala Phe Thr Gly Tyr
            20                  25                  30

Asn Met Asn Trp Val Lys Gln Thr Asn Gly Lys Ser Leu Glu Trp Ile
        35                  40                  45

Gly Ser Ile Asp Pro Tyr Tyr Gly Gly Ser Thr Tyr Asn Gln Lys Phe
50                  55                  60

Lys Asp Lys Ala Thr Leu Thr Val Asp Lys Ser Ser Thr Ala Tyr
65                  70                  75                  80

Met Gln Leu Lys Ser Leu Thr Ser Asp Asp Ser Ala Val Tyr Tyr Cys
                85                  90                  95

Ala Arg Ser Pro Gly Gly Asp Tyr Ala Met Asp Tyr Trp Gly Gln Gly
            100                 105                 110

Thr Ser Val Thr Val Ser Ser
            115

<210> SEQ ID NO 7
<211> LENGTH: 322
<212> TYPE: DNA
<213> ORGANISM: Mouse

<400> SEQUENCE: 7

```
gacatcaaga tgacccagtc tccatcttcc atgtatgcat ctgtaggaga gagagtcact      60
atcacttgta aggcgagtca gggcattaat agctattcag ctggttcca gcagaaacca     120
gggaaatctc ctaagaccct gatttatcgt ggaaatagat tggtggatgg ggtcccatca    180
aggttcagtg gcagtggatc tgggcaagat tattctctca ccatcagcag cctggagtat    240
gaagatatgg gaatttatta ttgtctacag tatgatgagt ttccgtacac gttcggaggg    300
gggaccaagc tggaaataaa ac                                             322
```

<210> SEQ ID NO 8
<211> LENGTH: 107
<212> TYPE: PRT
<213> ORGANISM: Mouse

<400> SEQUENCE: 8

Asp Ile Lys Met Thr Gln Ser Pro Ser Ser Met Tyr Ala Ser Val Gly
1               5                   10                  15

Glu Arg Val Thr Ile Thr Cys Lys Ala Ser Gln Gly Ile Asn Ser Tyr
            20                  25                  30

Ser Gly Trp Phe Gln Gln Lys Pro Gly Lys Ser Pro Lys Thr Leu Ile
        35                  40                  45

Tyr Arg Gly Asn Arg Leu Val Asp Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80

Glu Asp Met Gly Ile Tyr Tyr Cys Leu Gln Tyr Asp Glu Phe Pro Tyr
                85                  90                  95

Thr Phe Gly Gly Gly Thr Lys Leu Glu Ile Lys
            100                 105

<210> SEQ ID NO 9
<211> LENGTH: 354
<212> TYPE: DNA
<213> ORGANISM: Mouse

<400> SEQUENCE: 9

```
caggtccaac tgcagcagcc tggggctgag cttgtgaagc ctggacttc agtgaagctg       60
tcctgcaagg cttctggcta caacttcacc aactactgga taaactgggt gaagctgagg    120
cctggacaag gccttgagtg gattggagaa atttatcctg gtagtggtag tactaattac    180
aatgagaagt tcaagagcaa ggccacactg actgcagaca catcctccag cacagcctac    240
atgcaactca gcagcctggc atctgaagac tctgctctct attactgtgc aagagatggt    300
aactactatg ctatggacta ctggggtcaa ggaacctcag tcaccgtctc ctca          354
```

<210> SEQ ID NO 10
<211> LENGTH: 118
<212> TYPE: PRT
<213> ORGANISM: Mouse

<400> SEQUENCE: 10

```
Gln Val Gln Leu Gln Gln Pro Gly Ala Glu Leu Val Lys Pro Gly Thr
  1               5                  10                  15

Ser Val Lys Leu Ser Cys Lys Ala Ser Gly Tyr Asn Phe Thr Asn Tyr
             20                  25                  30

Trp Ile Asn Trp Val Lys Leu Arg Pro Gly Gln Gly Leu Glu Trp Ile
         35                  40                  45

Gly Glu Ile Tyr Pro Gly Ser Gly Ser Thr Asn Tyr Asn Glu Lys Phe
 50                  55                  60

Lys Ser Lys Ala Thr Leu Thr Ala Asp Thr Ser Ser Ser Thr Ala Tyr
 65                  70                  75                  80

Met Gln Leu Ser Ser Leu Ala Ser Glu Asp Ser Ala Leu Tyr Tyr Cys
             85                  90                  95

Ala Arg Asp Gly Asn Tyr Tyr Ala Met Asp Tyr Trp Gly Gln Gly Thr
            100                 105                 110

Ser Val Thr Val Ser Ser
            115
```

<210> SEQ ID NO 11
<211> LENGTH: 325
<212> TYPE: DNA
<213> ORGANISM: Mouse

<400> SEQUENCE: 11

```
gatatccaga tgacacagac tacatcctcc ctgtctgcct ctctgggaga cagagtcacc    60
atcacttgca gggcaagtca ggacattaac aattatttaa actggtatca acagaaacca   120
gatggaactg ttaaactcct gatctactac acatcagcat tacactcagg agtcccatca   180
aggttcagtg gcagtgggtc tggaacagat tattctctca ccattagcaa cctggaacaa   240
gaagatattg ccacttactt ttgccaacag ggtaatacgc ttcctccgta cacgttcgga   300
ggggggacca agctggaaat aaaac                                         325
```

<210> SEQ ID NO 12
<211> LENGTH: 108
<212> TYPE: PRT
<213> ORGANISM: Mouse

<400> SEQUENCE: 12

```
Asp Ile Gln Met Thr Gln Thr Thr Ser Ser Leu Ser Ala Ser Leu Gly
  1               5                  10                  15

Asp Arg Val Thr Ile Thr Cys Arg Ala Ser Gln Asp Ile Asn Asn Tyr
             20                  25                  30

Leu Asn Trp Tyr Gln Gln Lys Pro Asp Gly Thr Val Lys Leu Leu Ile
         35                  40                  45

Tyr Tyr Thr Ser Ala Leu His Ser Gly Val Pro Ser Arg Phe Ser Gly
 50                  55                  60

Ser Gly Ser Gly Thr Asp Tyr Ser Leu Thr Ile Ser Asn Leu Glu Gln
 65                  70                  75                  80

Glu Asp Ile Ala Thr Tyr Phe Cys Gln Gln Gly Asn Thr Leu Pro Pro
             85                  90                  95

Tyr Thr Phe Gly Gly Gly Thr Lys Leu Glu Ile Lys
            100                 105
```

<210> SEQ ID NO 13
<211> LENGTH: 351
<212> TYPE: DNA
<213> ORGANISM: Mouse

<400> SEQUENCE: 13

```
caggtgcagc tgaaggagtc aggacctggc ctggtggcgc cctcacagac tctgtccatc      60
acttgcactg tctctgggtt ttcattaacc agttatggtg tacactgggt tcgccagcct     120
ccaggaaagg gtctggagtg gctgggagta atatgggctg gtggattcac aaattataat     180
tcggctctca gtccagact gagcatcagc aaagacaact ccaagagcca agttctctta     240
aaaatgacca gtctgcaaac tgatgacaca gccatgtact actgtgccag agaggtagt     300
tcctattcta tggactattg gggtcaagga acctcagtca ccgtctcctc a              351
```

<210> SEQ ID NO 14
<211> LENGTH: 117
<212> TYPE: PRT
<213> ORGANISM: Mouse

<400> SEQUENCE: 14

Gln Val Gln Leu Lys Glu Ser Gly Pro Gly Leu Val Ala Pro Ser Gln
1               5                   10                  15

Thr Leu Ser Ile Thr Cys Thr Val Ser Gly Phe Ser Leu Thr Ser Tyr
            20                  25                  30

Gly Val His Trp Val Arg Gln Pro Pro Gly Lys Gly Leu Glu Trp Leu
        35                  40                  45

Gly Val Ile Trp Ala Gly Gly Phe Thr Asn Tyr Asn Ser Ala Leu Lys
    50                  55                  60

Ser Arg Leu Ser Ile Ser Lys Asp Asn Ser Lys Ser Gln Val Leu Leu
65                  70                  75                  80

Lys Met Thr Ser Leu Gln Thr Asp Asp Thr Ala Met Tyr Tyr Cys Ala
                85                  90                  95

Arg Arg Gly Ser Ser Tyr Ser Met Asp Tyr Trp Gly Gln Gly Thr Ser
            100                 105                 110

Val Thr Val Ser Ser
        115

<210> SEQ ID NO 15
<211> LENGTH: 318
<212> TYPE: DNA
<213> ORGANISM: Mouse

<400> SEQUENCE: 15

```
gaaattgtgc tctctcagtc tccagccatc acagctgcat ctctgggcca aaaggtcacc      60
atcacctgca gtgccagttc aaatgtaagt tacatccact ggtaccagca gaggtcaggc     120
acctccccca gaccatggat ttatgaaata tccaaactgg cttctggagt cccagttcgc     180
ttcagtggca gtgggtctgg gacctcttac tctctcacaa tcagcagcat ggaggctgaa     240
gatgctgcca tttattattg tcagcagtgg aattatcctc ttatcacgtt cggctcgggg     300
acaaagttgg aaatacaa                                                    318
```

<210> SEQ ID NO 16
<211> LENGTH: 106
<212> TYPE: PRT
<213> ORGANISM: Mouse

<400> SEQUENCE: 16

Glu Ile Val Leu Ser Gln Ser Pro Ala Ile Thr Ala Ala Ser Leu Gly
1               5                   10                  15

Gln Lys Val Thr Ile Thr Cys Ser Ala Ser Ser Asn Val Ser Tyr Ile
            20                  25                  30

His Trp Tyr Gln Gln Arg Ser Gly Thr Ser Pro Arg Pro Trp Ile Tyr
        35                  40                  45

Glu Ile Ser Lys Leu Ala Ser Gly Val Pro Val Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Ile Tyr Tyr Cys Gln Gln Trp Asn Tyr Pro Leu Ile Thr
                85                  90                  95

Phe Gly Ser Gly Thr Lys Leu Glu Ile Gln
            100                 105

<210> SEQ ID NO 17
<211> LENGTH: 354
<212> TYPE: DNA
<213> ORGANISM: Mouse

<400> SEQUENCE: 17
gaagtgaagc tggtggagtc tgggggaggc ttagtgaagc ctggagggtc cctgaaactc      60
tcctgtgcag cctctggatt cactttcagt agctatgcca tgtcttgggt tcgccagact     120
ccagagaaga ggctggagtg gtcgcttcc attagtactg gtgctagcgc ctactttcca      180
gacagtgtga agggccgatt caccatctcc agagataatg ccaggaacat cctgtacctg     240
caaatgagca gtctgaggtc tgaggacacg gccatgtatt attgtgcaag gattactacg     300
tctacctggt acttcgatgt ctggggcgca gggaccacgg tcaccgtctc ctca           354

<210> SEQ ID NO 18
<211> LENGTH: 118
<212> TYPE: PRT
<213> ORGANISM: Mouse

<400> SEQUENCE: 18

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Thr Pro Glu Lys Arg Leu Glu Trp Val
        35                  40                  45

Ala Ser Ile Ser Thr Gly Ala Ser Ala Tyr Phe Pro Asp Ser Val Lys
    50                  55                  60

Gly Arg Phe Thr Ile Ser Arg Asp Asn Ala Arg Asn Ile Leu Tyr Leu
65                  70                  75                  80

Gln Met Ser Ser Leu Arg Ser Glu Asp Thr Ala Met Tyr Tyr Cys Ala
                85                  90                  95

Arg Ile Thr Thr Ser Thr Trp Tyr Phe Asp Val Trp Gly Ala Gly Thr
            100                 105                 110

Thr Val Thr Val Ser Ser
            115

<210> SEQ ID NO 19
<211> LENGTH: 322
<212> TYPE: DNA
<213> ORGANISM: Mouse

<400> SEQUENCE: 19

```
gacatcaaga tgacccagtc tccatcttcc atgtatgcat ctctaggaga gagagtcact    60
atcacttgca aggcgagtca ggacattaat agttatttaa gctggttcca gcagaaacca   120
gggaaatctc ctaagaccct gatctatcgt gcaaacagat tggtagatgg ggtcccatca   180
aggttcagtg gcagtggatc tgggcaagat tattctctca ccatcagcag cctggagtat   240
gaagatatgg gaatttatta ttgtctacag tatgatgagt ttccgtacac gttcggaggg   300
gggaccaagc tggaaataaa ac                                            322
```

<210> SEQ ID NO 20
<211> LENGTH: 107
<212> TYPE: PRT
<213> ORGANISM: Mouse

<400> SEQUENCE: 20

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
            20                  25                  30

Leu Ser Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80

Glu Asp Met Gly Ile Tyr Tyr Cys Leu Gln Tyr Asp Glu Phe Pro Tyr
                85                  90                  95

Thr Phe Gly Gly Gly Thr Lys Leu Glu Ile Lys
            100                 105

<210> SEQ ID NO 21
<211> LENGTH: 106
<212> TYPE: PRT
<213> ORGANISM: Mouse
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (31)..(34)
<223> OTHER INFORMATION: Xaa can be any naturally occurring amino acid
<220> FEATURE:
<221> NAME/KEY: misc_feature
<222> LOCATION: (60)..(62)
<223> OTHER INFORMATION: Xaa can be any naturally occurring amino acid
<220> FEATURE:
<221> NAME/KEY: misc_feature
<222> LOCATION: (73)..(73)
<223> OTHER INFORMATION: Xaa can be any naturally occurring amino acid

<400> SEQUENCE: 21

Glu Val Lys Leu Val Glu Ser Gly Gly Xaa Gly Leu Val Lys Pro Gly
1               5                   10                  15

Gly Ser Leu Lys Leu Ser Cys Ala Ala Ser Gly Phe Thr Phe Xaa Xaa
            20                  25                  30

Xaa Xaa Ser Ser Tyr Ala Met Ser Trp Val Arg Gln Ile Pro Glu Lys
         35                  40                  45

Arg Leu Glu Trp Val Ala Ser Ile Ser Arg Gly Xaa Xaa Xaa Gly Thr
 50                  55                  60

Thr Tyr Tyr Pro Asp Ser Val Lys Xaa Gly Arg Phe Thr Ile Ser Arg
 65                  70                  75                  80

Asp Asn Val Arg Asn Ile Leu Tyr Leu Gln Met Ser Ser Leu Arg Ser
                 85                  90                  95

Glu Asp Thr Ala Met Tyr Tyr Cys Gly Arg
                100                 105

<210> SEQ ID NO 22
<211> LENGTH: 106
<212> TYPE: PRT
<213> ORGANISM: Mouse
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (31)..(34)
<223> OTHER INFORMATION: Xaa can be any naturally occurring amino acid
<220> FEATURE:
<221> NAME/KEY: misc_feature
<222> LOCATION: (60)..(62)
<223> OTHER INFORMATION: Xaa can be any naturally occurring amino acid
<220> FEATURE:
<221> NAME/KEY: misc_feature
<222> LOCATION: (73)..(73)
<223> OTHER INFORMATION: Xaa can be any naturally occurring amino acid

<400> SEQUENCE: 22

Glu Val Lys Leu Val Glu Ser Gly Gly Xaa Gly Leu Val Lys Pro Gly
 1               5                  10                  15

Gly Ser Leu Lys Leu Ser Cys Ala Ala Ser Gly Phe Ala Phe Xaa Xaa
                 20                  25                  30

Xaa Xaa Ser Ser Tyr Asp Met Ser Trp Val Arg Gln Thr Pro Glu Lys
         35                  40                  45

Arg Leu Glu Trp Val Ala Thr Ile Ser Ser Gly Xaa Xaa Xaa Ser Tyr
 50                  55                  60

Thr Tyr Tyr Pro Asp Ser Val Lys Xaa Gly Arg Phe Thr Ile Ser Arg
 65                  70                  75                  80

Asp Asn Ala Arg Asn Thr Leu Tyr Leu Gln Met Ser Ser Leu Arg Ser
                 85                  90                  95

Glu Asp Thr Ala Leu Tyr Tyr Cys Ala Arg
                100                 105

<210> SEQ ID NO 23
<211> LENGTH: 106
<212> TYPE: PRT
<213> ORGANISM: Homo sapiens
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (31)..(34)
<223> OTHER INFORMATION: Xaa can be any naturally occurring amino acid
<220> FEATURE:
<221> NAME/KEY: misc_feature
<222> LOCATION: (60)..(61)
<223> OTHER INFORMATION: Xaa can be any naturally occurring amino acid

```
<220> FEATURE:
<221> NAME/KEY: misc_feature
<222> LOCATION: (73)..(73)
<223> OTHER INFORMATION: Xaa can be any naturally occurring amino acid

<400> SEQUENCE: 23

Glu Val Gln Leu Val Glu Ser Gly Gly Xaa Gly Leu Val Gln Pro Gly
1               5                   10                  15

Gly Ser Leu Arg Leu Ser Cys Ala Ala Ser Gly Phe Thr Phe Xaa Xaa
            20                  25                  30

Xaa Xaa Ser Ser Tyr Ser Met Asn Trp Val Arg Gln Ala Pro Gly Lys
        35                  40                  45

Gly Leu Glu Trp Val Ser Tyr Ile Ser Ser Ser Xaa Xaa Ser Ser Thr
    50                  55                  60

Ile Tyr Tyr Ala Asp Ser Val Lys Xaa Gly Arg Phe Thr Ile Ser Arg
65                  70                  75                  80

Asp Asn Ala Lys Asn Ser Leu Tyr Leu Gln Met Asn Ser Leu Arg Ala
                85                  90                  95

Glu Asp Thr Ala Val Tyr Tyr Cys Ala Arg
            100                 105

<210> SEQ ID NO 24
<211> LENGTH: 106
<212> TYPE: PRT
<213> ORGANISM: Mouse
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (31)..(34)
<223> OTHER INFORMATION: Xaa can be any naturally occurring amino acid
<220> FEATURE:
<221> NAME/KEY: misc_feature
<222> LOCATION: (60)..(61)
<223> OTHER INFORMATION: Xaa can be any naturally occurring amino acid
<220> FEATURE:
<221> NAME/KEY: misc_feature
<222> LOCATION: (73)..(73)
<223> OTHER INFORMATION: Xaa can be any naturally occurring amino acid

<400> SEQUENCE: 24

Glu Val Gln Leu Gln Gln Ser Gly Pro Xaa Glu Leu Glu Lys Pro Gly
1               5                   10                  15

Ala Ser Val Lys Ile Ser Cys Lys Ala Ser Gly Phe Ala Phe Xaa Xaa
            20                  25                  30

Xaa Xaa Thr Gly Tyr Asn Met Asn Trp Val Lys Gln Thr Asn Gly Lys
        35                  40                  45

Ser Leu Glu Trp Ile Gly Ser Ile Asp Pro Tyr Xaa Xaa Tyr Gly Gly
    50                  55                  60

Ser Thr Tyr Asn Gln Lys Phe Lys Xaa Asp Lys Ala Thr Leu Thr Val
65                  70                  75                  80

Asp Lys Ser Ser Ser Thr Ala Tyr Met Gln Leu Lys Ser Leu Thr Ser
                85                  90                  95

Asp Asp Ser Ala Val Tyr Tyr Cys Ala Arg
            100                 105

<210> SEQ ID NO 25
<211> LENGTH: 106
<212> TYPE: PRT
<213> ORGANISM: Mouse
```

-continued

```
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (31)..(34)
<223> OTHER INFORMATION: Xaa can be any naturally occurring amino acid
<220> FEATURE:
<221> NAME/KEY: misc_feature
<222> LOCATION: (60)..(63)
<223> OTHER INFORMATION: Xaa can be any naturally occurring amino acid
<220> FEATURE:
<221> NAME/KEY: misc_feature
<222> LOCATION: (73)..(73)
<223> OTHER INFORMATION: Xaa can be any naturally occurring amino acid

<400> SEQUENCE: 25

Glu Phe Gln Leu Gln Gln Ser Gly Pro Xaa Glu Leu Val Lys Pro Gly
1               5                   10                  15

Ala Ser Val Lys Ile Ser Cys Lys Ala Ser Gly Tyr Ser Phe Xaa Xaa
            20                  25                  30

Xaa Xaa Thr Asp Tyr Asn Met Asn Trp Val Lys Gln Ser Asn Gly Lys
        35                  40                  45

Ser Leu Glu Trp Ile Gly Val Ile Asn Pro Asn Xaa Xaa Xaa Xaa Thr
    50                  55                  60

Thr Ser Tyr Asn Gln Lys Phe Lys Xaa Gly Lys Ala Thr Leu Thr Val
65                  70                  75                  80

Asp Gln Ser Ser Ser Thr Ala Tyr Met Gln Leu Asn Ser Leu Thr Ser
                85                  90                  95

Ser Asp Ser Ala Val Tyr Tyr Cys Ala Arg
            100                 105

<210> SEQ ID NO 26
<211> LENGTH: 106
<212> TYPE: PRT
<213> ORGANISM: Homo sapiens
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (31)..(34)
<223> OTHER INFORMATION: Xaa can be any naturally occurring amino acid
<220> FEATURE:
<221> NAME/KEY: misc_feature
<222> LOCATION: (60)..(61)
<223> OTHER INFORMATION: Xaa can be any naturally occurring amino acid
<220> FEATURE:
<221> NAME/KEY: misc_feature
<222> LOCATION: (73)..(73)
<223> OTHER INFORMATION: Xaa can be any naturally occurring amino acid

<400> SEQUENCE: 26

Gln Val Gln Leu Val Gln Ser Gly Ala Xaa Glu Val Lys Lys Pro Gly
1               5                   10                  15

Ala Ser Val Lys Val Ser Cys Lys Ala Ser Gly Tyr Thr Phe Xaa Xaa
            20                  25                  30

Xaa Xaa Thr Gly Tyr Tyr Met His Trp Val Arg Gln Ala Pro Gly Gln
        35                  40                  45

Gly Leu Glu Trp Met Gly Trp Ile Asn Pro Asn Xaa Xaa Ser Gly Gly
    50                  55                  60

Thr Asn Tyr Ala Gln Lys Phe Gln Xaa Gly Arg Val Thr Met Thr Arg
65                  70                  75                  80
```

Asp Thr Ser Ile Ser Thr Ala Tyr Met Glu Leu Ser Arg Leu Arg Ser
            85                  90                  95

Asp Asp Thr Ala Val Tyr Tyr Cys Ala Arg
            100                 105

<210> SEQ ID NO 27
<211> LENGTH: 106
<212> TYPE: PRT
<213> ORGANISM: Mouse
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (31)..(34)
<223> OTHER INFORMATION: Xaa can be any naturally occurring amino acid
<220> FEATURE:
<221> NAME/KEY: misc_feature
<222> LOCATION: (60)..(61)
<223> OTHER INFORMATION: Xaa can be any naturally occurring amino acid
<220> FEATURE:
<221> NAME/KEY: misc_feature
<222> LOCATION: (73)..(73)
<223> OTHER INFORMATION: Xaa can be any naturally occurring amino acid

<400> SEQUENCE: 27

Gln Val Gln Leu Gln Gln Pro Gly Ala Xaa Glu Leu Val Lys Pro Gly
1               5                   10                  15

Thr Ser Val Lys Leu Ser Cys Lys Ala Ser Gly Tyr Asn Phe Xaa Xaa
            20                  25                  30

Xaa Xaa Thr Asn Tyr Trp Ile Asn Trp Val Lys Leu Arg Pro Gly Gln
            35                  40                  45

Gly Leu Glu Trp Ile Gly Glu Ile Tyr Pro Gly Xaa Xaa Ser Gly Ser
        50                  55                  60

Thr Asn Tyr Asn Glu Lys Phe Lys Xaa Ser Lys Ala Thr Leu Thr Ala
65                  70                  75                  80

Asp Thr Ser Ser Ser Thr Ala Tyr Met Gln Leu Ser Ser Leu Ala Ser
            85                  90                  95

Glu Asp Ser Ala Leu Tyr Tyr Cys Ala Arg
            100                 105

<210> SEQ ID NO 28
<211> LENGTH: 106
<212> TYPE: PRT
<213> ORGANISM: Mouse
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (31)..(34)
<223> OTHER INFORMATION: Xaa can be any naturally occurring amino acid
<220> FEATURE:
<221> NAME/KEY: misc_feature
<222> LOCATION: (60)..(61)
<223> OTHER INFORMATION: Xaa can be any naturally occurring amino acid
<220> FEATURE:
<221> NAME/KEY: misc_feature
<222> LOCATION: (73)..(73)
<223> OTHER INFORMATION: Xaa can be any naturally occurring amino acid

<400> SEQUENCE: 28

```
Gln Val Gln Leu Gln Gln Pro Gly Ala Xaa Glu Leu Val Lys Pro Gly
1               5                   10                  15

Ala Ser Val Lys Met Ser Cys Lys Ala Ser Gly Tyr Thr Phe Xaa Xaa
            20                  25                  30

Xaa Xaa Thr Ser Tyr Trp Ile Thr Trp Val Lys Gln Arg Pro Gly Gln
        35                  40                  45

Gly Leu Glu Trp Ile Gly Asp Ile Tyr Pro Gly Xaa Xaa Ser Gly Ser
    50                  55                  60

Thr Asn Tyr Asn Glu Lys Phe Lys Xaa Ser Lys Ala Thr Leu Thr Val
65                  70                  75                  80

Asp Thr Ser Ser Ser Thr Ala Tyr Met Gln Leu Ser Ser Leu Thr Ser
                85                  90                  95

Glu Asp Ser Ala Val Tyr Tyr Cys Ala Arg
            100                 105
```

<210> SEQ ID NO 29
<211> LENGTH: 106
<212> TYPE: PRT
<213> ORGANISM: Homo sapiens
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (31)..(34)
<223> OTHER INFORMATION: Xaa can be any naturally occurring amino acid
<220> FEATURE:
<221> NAME/KEY: misc_feature
<222> LOCATION: (60)..(61)
<223> OTHER INFORMATION: Xaa can be any naturally occurring amino acid
<220> FEATURE:
<221> NAME/KEY: misc_feature
<222> LOCATION: (73)..(73)
<223> OTHER INFORMATION: Xaa can be any naturally occurring amino acid

<400> SEQUENCE: 29

```
Gln Val Gln Leu Val Gln Ser Gly Ala Xaa Glu Val Lys Lys Pro Gly
1               5                   10                  15

Ala Ser Val Lys Val Ser Cys Lys Ala Ser Gly Tyr Thr Phe Xaa Xaa
            20                  25                  30

Xaa Xaa Thr Ser Tyr Tyr Met His Trp Val Arg Gln Ala Pro Gly Gln
        35                  40                  45

Gly Leu Glu Trp Met Gly Ile Ile Asn Pro Ser Xaa Xaa Gly Gly Ser
    50                  55                  60

Thr Ser Tyr Ala Gln Lys Phe Gln Xaa Gly Arg Val Thr Met Thr Arg
65                  70                  75                  80

Asp Thr Ser Thr Ser Thr Val Tyr Met Glu Leu Ser Ser Leu Arg Ser
                85                  90                  95

Glu Asp Thr Ala Val Tyr Tyr Cys Ala Arg
            100                 105
```

<210> SEQ ID NO 30
<211> LENGTH: 106
<212> TYPE: PRT
<213> ORGANISM: Mouse
<220> FEATURE:
<221> NAME/KEY: misc_feature
<222> LOCATION: (10)..(10)
<223> OTHER INFORMATION: Xaa can be any naturally occurring amino acid -continued

```
<220> FEATURE:
<221> NAME/KEY: misc_feature
<222> LOCATION: (31)..(34)
<223> OTHER INFORMATION: Xaa can be any naturally occurring amino acid
<220> FEATURE:
<221> NAME/KEY: misc_feature
<222> LOCATION: (60)..(62)
<223> OTHER INFORMATION: Xaa can be any naturally occurring amino acid
<220> FEATURE:
<221> NAME/KEY: misc_feature
<222> LOCATION: (73)..(73)
<223> OTHER INFORMATION: Xaa can be any naturally occurring amino acid

<400> SEQUENCE: 30

Glu Val Lys Leu Val Glu Ser Gly Gly Xaa Gly Leu Val Lys Pro Gly
1               5                   10                  15

Gly Ser Leu Lys Leu Ser Cys Ala Ala Ser Gly Phe Thr Phe Xaa Xaa
            20                  25                  30

Xaa Xaa Ser Ser Tyr Ala Met Ser Trp Val Arg Gln Thr Pro Glu Lys
        35                  40                  45

Arg Leu Glu Trp Val Ala Ser Ile Ser Thr Gly Xaa Xaa Xaa Ala Ser
50                  55                  60

Thr Tyr Phe Pro Asp Ser Val Lys Xaa Gly Arg Phe Thr Ile Ser Arg
65                  70                  75                  80

Asp Asn Ala Arg Asn Ile Leu Tyr Leu Gln Met Ser Ser Leu Arg Ser
                85                  90                  95

Glu Asp Thr Ala Met Tyr Tyr Cys Ala Arg
            100                 105

<210> SEQ ID NO 31
<211> LENGTH: 106
<212> TYPE: PRT
<213> ORGANISM: Mouse
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (31)..(34)
<223> OTHER INFORMATION: Xaa can be any naturally occurring amino acid
<220> FEATURE:
<221> NAME/KEY: misc_feature
<222> LOCATION: (60)..(61)
<223> OTHER INFORMATION: Xaa can be any naturally occurring amino acid
<220> FEATURE:
<221> NAME/KEY: misc_feature
<222> LOCATION: (73)..(73)
<223> OTHER INFORMATION: Xaa can be any naturally occurring amino acid

<400> SEQUENCE: 31

Glu Val Lys Leu Val Glu Ser Gly Gly Xaa Gly Leu Val Lys Pro Gly
1               5                   10                  15

Gly Ser Leu Lys Leu Ser Cys Ala Ala Ser Gly Phe Ala Phe Xaa Xaa
            20                  25                  30

Xaa Xaa Ser Ser Tyr Asp Met Ser Trp Val Arg Gln Thr Pro Glu Lys
        35                  40                  45

Arg Leu Glu Trp Val Ala Thr Ile Ser Ser Gly Xaa Xaa Gly Ala Ser
50                  55                  60

Thr Tyr Tyr Pro Asp Ser Val Lys Xaa Gly Arg Phe Thr Ile Ser Arg
65                  70                  75                  80
```

Asp Asn Ala Arg Asn Thr Leu Tyr Leu Gln Met Ser Ser Leu Arg Ser
            85                  90                  95

Glu Asp Thr Ala Leu Tyr Tyr Cys Ala Arg
            100                 105

<210> SEQ ID NO 32
<211> LENGTH: 106
<212> TYPE: PRT
<213> ORGANISM: Homo sapiens
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (31)..(34)
<223> OTHER INFORMATION: Xaa can be any naturally occurring amino acid
<220> FEATURE:
<221> NAME/KEY: misc_feature
<222> LOCATION: (60)..(61)
<223> OTHER INFORMATION: Xaa can be any naturally occurring amino acid
<220> FEATURE:
<221> NAME/KEY: misc_feature
<222> LOCATION: (73)..(73)
<223> OTHER INFORMATION: Xaa can be any naturally occurring amino acid

<400> SEQUENCE: 32

Glu Val Gln Leu Val Glu Ser Gly Gly Xaa Gly Leu Val Gln Pro Gly
1               5                   10                  15

Gly Ser Leu Arg Leu Ser Cys Ala Ala Ser Gly Phe Thr Phe Xaa Xaa
            20                  25                  30

Xaa Xaa Ser Ser Tyr Ala Met Ser Trp Val Arg Gln Ala Pro Gly Lys
            35                  40                  45

Gly Leu Glu Trp Val Ser Ala Ile Ser Gly Ser Xaa Xaa Gly Gly Ser
        50                  55                  60

Thr Tyr Tyr Ala Asp Ser Val Lys Xaa Gly Arg Phe Thr Ile Ser Arg
65                  70                  75                  80

Asp Asn Ser Lys Asn Thr Leu Tyr Leu Gln Met Asn Ser Leu Arg Ala
            85                  90                  95

Glu Asp Thr Ala Val Tyr Tyr Cys Ala Lys
            100                 105

<210> SEQ ID NO 33
<211> LENGTH: 106
<212> TYPE: PRT
<213> ORGANISM: Mouse
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (31)..(34)
<223> OTHER INFORMATION: Xaa can be any naturally occurring amino acid
<220> FEATURE:
<221> NAME/KEY: misc_feature
<222> LOCATION: (60)..(62)
<223> OTHER INFORMATION: Xaa can be any naturally occurring amino acid
<220> FEATURE:
<221> NAME/KEY: misc_feature
<222> LOCATION: (73)..(73)
<223> OTHER INFORMATION: Xaa can be any naturally occurring amino acid

<400> SEQUENCE: 33

Gln Val Gln Leu Lys Glu Ser Gly Pro Xaa Gly Leu Val Ala Pro Ser
1               5                   10                  15

Gln Thr Leu Ser Ile Thr Cys Thr Val Ser Gly Phe Ser Leu Xaa Xaa
            20                  25                  30

Xaa Xaa Thr Ser Tyr Gly Val His Trp Val Arg Gln Pro Pro Gly Lys
        35                  40                  45

Gly Leu Glu Trp Leu Gly Val Ile Trp Ala Gly Xaa Xaa Xaa Gly Phe
    50                  55                  60

Thr Asn Tyr Asn Ser Ala Leu Lys Xaa Ser Arg Leu Ser Ile Ser Lys
65                  70                  75                  80

Asp Asn Ser Lys Ser Gln Val Leu Leu Lys Met Thr Ser Leu Gln Thr
                85                  90                  95

Asp Asp Thr Ala Met Tyr Tyr Cys Ala Arg
            100                 105

<210> SEQ ID NO 34
<211> LENGTH: 106
<212> TYPE: PRT
<213> ORGANISM: Mouse
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (31)..(34)
<223> OTHER INFORMATION: Xaa can be any naturally occurring amino acid
<220> FEATURE:
<221> NAME/KEY: misc_feature
<222> LOCATION: (60)..(62)
<223> OTHER INFORMATION: Xaa can be any naturally occurring amino acid
<220> FEATURE:
<221> NAME/KEY: misc_feature
<222> LOCATION: (73)..(73)
<223> OTHER INFORMATION: Xaa can be any naturally occurring amino acid

<400> SEQUENCE: 34

Gln Val Gln Leu Lys Glu Ser Gly Pro Xaa Gly Leu Val Ala Pro Ser
1               5                   10                  15

Gln Ser Leu Ser Ile Thr Cys Thr Val Ser Gly Phe Ser Leu Xaa Xaa
            20                  25                  30

Xaa Xaa Thr Ser Tyr Gly Val His Trp Val Arg Gln Pro Pro Gly Lys
        35                  40                  45

Gly Leu Glu Trp Leu Gly Val Ile Trp Ala Gly Xaa Xaa Xaa Gly Ser
    50                  55                  60

Thr Asn Tyr Asn Ser Ala Leu Met Xaa Ser Arg Leu Ser Ile Ser Lys
65                  70                  75                  80

Asp Asn Ser Lys Ser Gln Val Phe Leu Lys Met Asn Ser Leu Gln Thr
                85                  90                  95

Asp Asp Thr Ala Met Tyr Tyr Cys Ala Arg
            100                 105

<210> SEQ ID NO 35
<211> LENGTH: 106
<212> TYPE: PRT
<213> ORGANISM: Homo sapiens
<220> FEATURE:
<221> NAME/KEY: misc_feature
<222> LOCATION: (10)..(10)
<223> OTHER INFORMATION: Xaa can be any naturally occurring amino acid

```
<220> FEATURE:
<221> NAME/KEY: misc_feature
<222> LOCATION: (31)..(34)
<223> OTHER INFORMATION: Xaa can be any naturally occurring amino acid
<220> FEATURE:
<221> NAME/KEY: misc_feature
<222> LOCATION: (60)..(62)
<223> OTHER INFORMATION: Xaa can be any naturally occurring amino acid
<220> FEATURE:
<221> NAME/KEY: misc_feature
<222> LOCATION: (73)..(73)
<223> OTHER INFORMATION: Xaa can be any naturally occurring amino acid

<400> SEQUENCE: 35

Gln Val Gln Leu Gln Glu Ser Gly Pro Xaa Gly Leu Val Lys Pro Ser
1               5                   10                  15

Gln Thr Leu Ser Leu Thr Cys Ala Val Tyr Gly Gly Ser Phe Xaa Xaa
            20                  25                  30

Xaa Xaa Ser Gly Tyr Tyr Trp Ser Trp Ile Arg Gln Pro Pro Gly Lys
        35                  40                  45

Gly Leu Glu Trp Ile Gly Glu Ile Asn His Ser Xaa Xaa Xaa Gly Ser
    50                  55                  60

Thr Asn Tyr Asn Pro Ser Leu Lys Xaa Ser Arg Val Thr Ile Ser Val
65                  70                  75                  80

Asp Thr Ser Lys Asn Gln Phe Ser Leu Lys Leu Ser Ser Val Thr Ala
                85                  90                  95

Ala Asp Thr Ala Val Tyr Tyr Cys Ala Arg
            100                 105

<210> SEQ ID NO 36
<211> LENGTH: 406
<212> TYPE: PRT
<213> ORGANISM: Homo sapiens

<400> SEQUENCE: 36

Met His Arg Pro Arg Arg Arg Gly Thr Arg Pro Pro Leu Leu Ala Leu
1               5                   10                  15

Leu Ala Ala Leu Leu Leu Ala Ala Arg Gly Ala Ala Ala Gln Glu Thr
            20                  25                  30

Glu Leu Ser Val Ser Ala Glu Leu Val Pro Thr Ser Ser Trp Asn Ile
        35                  40                  45

Ser Ser Glu Leu Asn Lys Asp Ser Tyr Leu Thr Leu Asp Glu Pro Met
    50                  55                  60

Asn Asn Ile Thr Thr Ser Leu Gly Gln Thr Ala Glu Leu His Cys Lys
65                  70                  75                  80

Val Ser Gly Asn Pro Pro Pro Thr Ile Arg Trp Phe Lys Asn Asp Ala
                85                  90                  95

Pro Val Val Gln Glu Pro Arg Arg Leu Ser Phe Arg Ser Thr Ile Tyr
            100                 105                 110

Gly Ser Arg Leu Arg Ile Arg Asn Leu Asp Thr Thr Asp Thr Gly Tyr
        115                 120                 125

Phe Gln Cys Val Ala Thr Asn Gly Lys Glu Val Val Ser Ser Thr Gly
    130                 135                 140

Val Leu Phe Val Lys Phe Gly Pro Pro Thr Ala Ser Pro Gly Tyr
145                 150                 155                 160

Ser Asp Glu Tyr Glu Glu Asp Gly Phe Cys Gln Pro Tyr Arg Gly Ile
                165                 170                 175

Ala Cys Ala Arg Phe Ile Gly Asn Arg Thr Val Tyr Met Glu Ser Leu
            180                 185                 190
```

```
His Met Gln Gly Glu Ile Glu Asn Gln Ile Thr Ala Ala Phe Thr Met
            195                 200                 205

Ile Gly Thr Ser Ser His Leu Ser Asp Lys Cys Ser Gln Phe Ala Ile
210                 215                 220

Pro Ser Leu Cys His Tyr Ala Phe Pro Tyr Cys Asp Glu Thr Ser Ser
225                 230                 235                 240

Val Pro Lys Pro Arg Asp Leu Cys Arg Asp Glu Cys Glu Ile Leu Glu
                245                 250                 255

Asn Val Leu Cys Gln Thr Glu Tyr Ile Phe Ala Arg Ser Asn Pro Met
            260                 265                 270

Ile Leu Met Arg Leu Lys Leu Pro Asn Cys Glu Asp Leu Pro Gln Pro
        275                 280                 285

Glu Ser Pro Glu Ala Ala Asn Cys Ile Arg Ile Gly Ile Pro Met Ala
290                 295                 300

Asp Pro Ile Asn Lys Asn His Lys Cys Tyr Asn Ser Thr Gly Val Asp
305                 310                 315                 320

Tyr Arg Gly Thr Val Ser Val Thr Lys Ser Gly Arg Gln Cys Gln Pro
                325                 330                 335

Trp Asn Ser Gln Tyr Pro His Thr His Thr Phe Thr Ala Leu Arg Phe
            340                 345                 350

Pro Glu Leu Asn Gly Gly His Ser Tyr Cys Arg Asn Pro Gly Asn Gln
        355                 360                 365

Lys Glu Ala Pro Trp Cys Phe Thr Leu Asp Glu Asn Phe Lys Ser Asp
    370                 375                 380

Leu Cys Asp Ile Pro Ala Cys Asp Ser Lys Asp Ser Lys Glu Lys Asn
385                 390                 395                 400

Lys Met Glu Ile Leu Tyr
                405

<210> SEQ ID NO 37
<211> LENGTH: 406
<212> TYPE: PRT
<213> ORGANISM: Murine

<400> SEQUENCE: 37

Met His Arg Pro Arg Arg Arg Gly Thr Arg Pro Pro Leu Ala Leu
1               5                   10                  15

Leu Ala Leu Leu Leu Ala Ala Arg Gly Ala Asp Ala Gln Glu Thr
            20                  25                  30

Glu Leu Ser Val Ser Ala Glu Leu Val Pro Thr Ser Ser Trp Asn Thr
            35                  40                  45

Ser Ser Glu Ile Asp Lys Gly Ser Tyr Leu Thr Leu Asp Glu Pro Met
    50                  55                  60

Asn Asn Ile Thr Thr Ser Leu Gly Gln Thr Ala Glu Leu His Cys Lys
65                  70                  75                  80

Val Ser Gly Asn Pro Pro Pro Ser Ile Arg Trp Phe Lys Asn Asp Ala
                85                  90                  95

Pro Val Val Gln Glu Pro Arg Arg Ile Ser Phe Arg Ala Thr Asn Tyr
            100                 105                 110

Gly Ser Arg Leu Arg Ile Arg Asn Leu Asp Thr Thr Asp Thr Gly Tyr
        115                 120                 125

Phe Gln Cys Val Ala Thr Asn Gly Lys Lys Val Val Ser Thr Thr Gly
    130                 135                 140

Val Leu Phe Val Lys Phe Gly Pro Pro Pro Thr Ala Ser Pro Gly Ser
145                 150                 155                 160
```

-continued

```
Ser Asp Glu Tyr Glu Asp Gly Phe Cys Gln Pro Tyr Arg Gly Ile
            165             170             175

Ala Cys Ala Arg Phe Ile Gly Asn Arg Thr Val Tyr Met Glu Ser Leu
            180             185             190

His Met Gln Gly Glu Ile Glu Asn Gln Ile Thr Ala Ala Phe Thr Met
        195             200             205

Ile Gly Thr Ser Ser His Leu Ser Asp Lys Cys Ser Gln Phe Ala Ile
        210             215             220

Pro Ser Leu Cys His Tyr Ala Phe Pro Tyr Cys Asp Glu Thr Ser Ser
225             230             235             240

Val Pro Lys Pro Arg Asp Leu Cys Arg Asp Glu Cys Glu Val Leu Glu
            245             250             255

Asn Val Leu Cys Gln Thr Glu Tyr Ile Phe Ala Arg Ser Asn Pro Met
            260             265             270

Ile Leu Met Arg Leu Lys Leu Pro Asn Cys Glu Asp Leu Pro Gln Pro
        275             280             285

Glu Ser Pro Glu Ala Ala Asn Cys Ile Arg Ile Gly Ile Pro Met Ala
        290             295             300

Asp Pro Ile Asn Lys Asn His Lys Cys Tyr Asn Ser Thr Gly Val Asp
305             310             315             320

Tyr Arg Gly Thr Val Ser Val Thr Lys Ser Gly Arg Gln Cys Gln Pro
            325             330             335

Trp Asn Ser Gln Tyr Pro His Ser His Thr Phe Thr Ala Leu Arg Phe
            340             345             350

Pro Glu Leu Asn Gly Gly His Ser Tyr Cys Arg Asn Pro Gly Asn Gln
            355             360             365

Lys Glu Ala Pro Trp Cys Phe Thr Leu Asp Glu Asn Phe Lys Ser Asp
    370             375             380

Leu Cys Asp Ile Pro Ala Cys Asp Ser Lys Asp Ser Lys Glu Lys Asn
385             390             395             400

Lys Met Glu Ile Leu Tyr
            405
```